(12) United States Patent
Windmiller et al.

(10) Patent No.: US 12,369,830 B2
(45) Date of Patent: *Jul. 29, 2025

(54) METHODS FOR ACHIEVING AN ISOLATED ELECTRICAL INTERFACE BETWEEN AN ANTERIOR SURFACE OF A MICRONEEDLE STRUCTURE AND A POSTERIOR SURFACE OF A SUPPORT STRUCTURE

(71) Applicant: Biolinq Incorporated, San Diego, CA (US)

(72) Inventors: Joshua Windmiller, San Diego, CA (US); James Patrick McCanna, Pleasanton, CA (US); Jared Rylan Tangney, Encinitas, CA (US)

(73) Assignee: Biolinq Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/824,598

(22) Filed: Sep. 4, 2024

(65) Prior Publication Data
US 2024/0423526 A1    Dec. 26, 2024

Related U.S. Application Data

(63) Continuation of application No. 15/913,709, filed on Mar. 6, 2018, now Pat. No. 12,109,032.
(Continued)

(51) Int. Cl.
*A61B 5/296*    (2021.01)
*A61B 5/00*    (2006.01)
*A61B 5/1486*    (2006.01)

(52) U.S. Cl.
CPC .......... *A61B 5/296* (2021.01); *A61B 5/14865* (2013.01); *A61B 5/6848* (2013.01); *A61B 5/685* (2013.01)

(58) Field of Classification Search
None
See application file for complete search history.

(56) References Cited

U.S. PATENT DOCUMENTS

| 3,964,482 A | 6/1976 | Gerstel et al. |
| 4,305,401 A | 12/1981 | Reissmueller et al. |

(Continued)

FOREIGN PATENT DOCUMENTS

| CN | 101068591 A | 11/2007 |
| CN | 112617822 A | 4/2021 |

(Continued)

OTHER PUBLICATIONS

Al Hayek et al., "Patient Satisfaction and Clinical Efficacy of Novel Blood Glucose Meters Featuring Color Range Indicators in Patients With Type 2 Diabetes: A Prospective Study" Cureus Oct. 27, 2020; 12(10):e11195. 8 pages.

(Continued)

*Primary Examiner* — Jacqueline Cheng
*Assistant Examiner* — Jairo H Portillo
(74) *Attorney, Agent, or Firm* — Cooley LLP

(57) ABSTRACT

A method for circumscribing an insulating barrier region around a singular conductive microneedle structure or plurality of conductive microneedle structures adhered to a fixed substrate for the purpose of spatially defining a conduit for the routing of an electrical signal from the surface of said microneedle or microneedles to the posterior surface of the substrate is disclosed herein. A microneedle-based electrochemical biosensors structure comprises a substrate, a microneedle biosensor, a primary electrically conductive element, a secondary electrically conductive element and an electrically insulative annular barrier.

30 Claims, 9 Drawing Sheets

Related U.S. Application Data

(60) Provisional application No. 62/470,204, filed on Mar. 11, 2017.

(56) References Cited

U.S. PATENT DOCUMENTS

| | | |
|---|---|---|
| 4,323,996 A | 4/1982 | Ganter |
| 4,407,295 A | 10/1983 | Steuer et al. |
| 4,450,842 A | 5/1984 | Zick et al. |
| 4,908,117 A | 3/1990 | Kinlen et al. |
| 4,969,468 A | 11/1990 | Byers et al. |
| 5,035,711 A | 7/1991 | Aoki et al. |
| 5,131,390 A | 7/1992 | Sakaguchi et al. |
| 5,279,543 A | 1/1994 | Glikfeld et al. |
| 5,286,364 A | 2/1994 | Yacynych et al. |
| 5,540,828 A | 7/1996 | Yacynych |
| 5,730,714 A | 3/1998 | Guy et al. |
| 5,766,132 A | 6/1998 | Yasukawa et al. |
| 5,832,410 A | 11/1998 | Lin et al. |
| 5,869,078 A | 2/1999 | Baudino |
| 5,953,306 A | 9/1999 | Yi |
| 6,036,055 A | 3/2000 | Mogadam et al. |
| 6,091,975 A | 7/2000 | Daddona et al. |
| 6,132,449 A | 10/2000 | Lum et al. |
| 6,132,499 A | 10/2000 | Wong et al. |
| 6,132,755 A | 10/2000 | Eicher et al. |
| 6,139,718 A | 10/2000 | Kurnik et al. |
| 6,175,752 B1 | 1/2001 | Say et al. |
| 6,269,053 B1 | 7/2001 | Kawata et al. |
| 6,284,126 B1 | 9/2001 | Kurnik et al. |
| 6,364,890 B1 | 4/2002 | Lum et al. |
| 6,413,396 B1 | 7/2002 | Yang et al. |
| 6,465,091 B1 | 10/2002 | Ou-Yang |
| 6,471,903 B2 | 10/2002 | Sherman et al. |
| 6,527,762 B1 | 3/2003 | Santini, Jr. et al. |
| 6,551,849 B1 | 4/2003 | Kenney |
| 6,587,705 B1 | 7/2003 | Kim et al. |
| 6,599,408 B1 | 7/2003 | Chan et al. |
| 6,603,987 B2 | 8/2003 | Whitson |
| 6,611,707 B1 | 8/2003 | Prausnitz et al. |
| 6,793,789 B2 | 9/2004 | Choi et al. |
| 6,801,041 B2 | 10/2004 | Karinka et al. |
| 6,814,845 B2 | 11/2004 | Wilson et al. |
| 6,862,466 B2 | 3/2005 | Ackerman |
| 6,908,453 B2 | 6/2005 | Fleming et al. |
| 7,081,195 B2 | 7/2006 | Simpson et al. |
| 7,097,776 B2 | 8/2006 | Govinda Raju |
| 7,132,054 B1 | 11/2006 | Kravitz et al. |
| 7,183,068 B2 | 2/2007 | Burson et al. |
| 7,262,068 B2 | 8/2007 | Roy et al. |
| 7,343,188 B2 | 3/2008 | Sohrab |
| 7,344,499 B1 | 3/2008 | Prausnitz et al. |
| 7,366,556 B2 | 4/2008 | Brister et al. |
| 7,415,299 B2 | 8/2008 | Zimmermann et al. |
| 7,429,333 B2 | 9/2008 | Chiou et al. |
| 7,456,112 B2 | 11/2008 | Lee |
| 7,471,972 B2 | 12/2008 | Rhodes et al. |
| 7,473,244 B2 | 1/2009 | Frazier et al. |
| 7,493,232 B1 | 2/2009 | Surina |
| 7,534,330 B2 | 5/2009 | Yu et al. |
| 7,583,990 B2 | 9/2009 | Goode, Jr. et al. |
| 7,599,726 B2 | 10/2009 | Goode, Jr. et al. |
| 7,613,491 B2 | 11/2009 | Boock et al. |
| 7,645,263 B2 | 1/2010 | Angel et al. |
| 7,715,893 B2 | 5/2010 | Kamath et al. |
| 7,725,148 B2 | 5/2010 | Shah et al. |
| 7,768,408 B2 | 8/2010 | Reggiardo et al. |
| 7,778,680 B2 | 8/2010 | Goode, Jr. et al. |
| 7,797,028 B2 | 9/2010 | Goode, Jr. et al. |
| 7,811,231 B2 | 10/2010 | Jin et al. |
| 7,837,654 B2 | 11/2010 | Shumate et al. |
| 7,885,697 B2 | 2/2011 | Brister et al. |
| 7,905,833 B2 | 3/2011 | Brister et al. |
| 7,917,186 B2 | 3/2011 | Kamath et al. |
| 7,949,382 B2 | 5/2011 | Jina |
| 7,959,569 B2 | 6/2011 | Goode et al. |
| 8,005,526 B2 | 8/2011 | Martin et al. |
| 8,010,174 B2 | 8/2011 | Goode, Jr. et al. |
| 8,022,292 B2 | 9/2011 | Arianpour et al. |
| 8,064,977 B2 | 11/2011 | Boock et al. |
| 8,088,321 B2 | 1/2012 | Ferguson et al. |
| 8,094,009 B2 | 1/2012 | Allen et al. |
| 8,108,023 B2 | 1/2012 | Mir et al. |
| 8,110,079 B2 | 2/2012 | Gooding et al. |
| 8,125,331 B2 | 2/2012 | Allen et al. |
| 8,130,095 B2 | 3/2012 | Allen et al. |
| 8,160,665 B2 | 4/2012 | Mischler et al. |
| 8,160,671 B2 | 4/2012 | Kamath et al. |
| 8,160,834 B2 | 4/2012 | Liang et al. |
| 8,162,901 B2 | 4/2012 | Gonnelli et al. |
| RE43,399 E | 5/2012 | Simpson et al. |
| 8,216,138 B1 | 7/2012 | McGarraugh |
| 8,236,368 B2 | 8/2012 | Jung et al. |
| 8,249,684 B2 | 8/2012 | Kamath et al. |
| 8,257,324 B2 | 9/2012 | Prausnitz et al. |
| 8,280,475 B2 | 10/2012 | Brister et al. |
| 8,280,476 B2 | 10/2012 | Jina |
| 8,284,046 B2 | 10/2012 | Allen et al. |
| 8,287,453 B2 | 10/2012 | Li et al. |
| 8,308,960 B2 | 11/2012 | Kalvesten et al. |
| 8,346,335 B2 | 1/2013 | Harper et al. |
| 8,376,945 B2 | 2/2013 | Hayter et al. |
| 8,386,004 B2 | 2/2013 | Kamath et al. |
| 8,423,114 B2 | 4/2013 | Simpson et al. |
| 8,428,678 B2 | 4/2013 | Kamath et al. |
| 8,452,369 B2 | 5/2013 | Huys et al. |
| 8,463,350 B2 | 6/2013 | Kamath et al. |
| 8,483,793 B2 | 7/2013 | Simpson et al. |
| 8,506,529 B1 | 8/2013 | Yang |
| 8,548,553 B2 | 10/2013 | Kamath et al. |
| 8,565,848 B2 | 10/2013 | Brister et al. |
| 8,574,165 B2 | 11/2013 | Marsh |
| 8,617,069 B2 | 12/2013 | Bernstein et al. |
| RE44,695 E | 1/2014 | Simpson et al. |
| 8,626,257 B2 | 1/2014 | Li et al. |
| 8,637,351 B2 | 1/2014 | Kalvesten et al. |
| 8,660,628 B2 | 2/2014 | Wang et al. |
| 8,700,114 B2 | 4/2014 | Gottlieb et al. |
| 8,708,966 B2 | 4/2014 | Allen et al. |
| 8,798,799 B2 | 8/2014 | Deo et al. |
| 8,815,070 B2 | 8/2014 | Wang et al. |
| 8,870,763 B2 | 10/2014 | Yang et al. |
| 8,882,665 B2 | 11/2014 | Yang et al. |
| 9,008,743 B2 | 4/2015 | Hayter et al. |
| 9,008,745 B2 | 4/2015 | Pushpala et al. |
| 9,055,901 B2 | 6/2015 | Brister et al. |
| 9,125,625 B2 | 9/2015 | Wang et al. |
| 9,182,368 B2 | 11/2015 | Pushpala et al. |
| 9,234,872 B2 | 1/2016 | Homyk et al. |
| 9,248,273 B2 | 2/2016 | Guvanasen et al. |
| 9,332,934 B2 | 5/2016 | Hayter et al. |
| 9,336,423 B2 | 5/2016 | Goodnow et al. |
| 9,357,951 B2 | 6/2016 | Simpson et al. |
| 9,386,954 B2 | 7/2016 | Saini et al. |
| 9,387,000 B2 | 7/2016 | Corrie et al. |
| 9,414,778 B2 | 8/2016 | Mao et al. |
| 9,420,965 B2 | 8/2016 | Brauker et al. |
| 9,532,741 B2 | 1/2017 | Brauker et al. |
| 9,551,698 B2 | 1/2017 | Huys et al. |
| 9,662,056 B2 | 5/2017 | Budiman et al. |
| 9,737,247 B2 | 8/2017 | Wang et al. |
| 9,743,870 B2 | 8/2017 | Wang et al. |
| 9,743,871 B2 | 8/2017 | Simpson et al. |
| 9,757,061 B2 | 9/2017 | Shults et al. |
| 9,770,211 B2 | 9/2017 | Hayter et al. |
| 9,804,114 B2 | 10/2017 | Rhodes et al. |
| 9,933,387 B1 | 4/2018 | McCanna et al. |
| 9,958,409 B2 | 5/2018 | Gerber et al. |
| 10,022,076 B2 | 7/2018 | Hoss et al. |
| 10,039,480 B2 | 8/2018 | Brauker et al. |
| 10,046,114 B1 | 8/2018 | Biederman et al. |
| 10,052,055 B2 | 8/2018 | Li et al. |
| 10,092,207 B1 | 10/2018 | Windmiller |
| 10,136,846 B2 | 11/2018 | Wang et al. |
| 10,173,042 B2 | 1/2019 | Pushpala et al. |

(56) References Cited

U.S. PATENT DOCUMENTS

| | | | |
|---|---|---|---|
| 10,182,748 B2 | 1/2019 | Catt et al. |
| 10,188,333 B2 | 1/2019 | Kamath et al. |
| 10,228,341 B2 | 3/2019 | Katsuki et al. |
| 10,299,712 B2 | 5/2019 | Brister et al. |
| 10,327,678 B2 | 6/2019 | Gottlieb et al. |
| 10,492,708 B1 | 12/2019 | Windmiller |
| D875,254 S | 2/2020 | Cooke et al. |
| 10,549,080 B2 | 2/2020 | Pushpala et al. |
| 10,610,103 B2 | 4/2020 | Brister et al. |
| 10,709,332 B2 | 7/2020 | Brister et al. |
| 10,743,800 B2 | 8/2020 | Larvenz et al. |
| 10,780,222 B2 | 9/2020 | Ward et al. |
| 10,820,860 B2 | 11/2020 | Pushpala et al. |
| 10,881,334 B2 | 1/2021 | Facchinetti et al. |
| 10,932,700 B2 | 3/2021 | Simpson et al. |
| 10,983,083 B2 | 4/2021 | Harding et al. |
| 11,020,026 B2 | 6/2021 | Boock et al. |
| 11,035,872 B2 | 6/2021 | Boutelle et al. |
| 11,045,142 B1 | 6/2021 | Windmiller et al. |
| 11,051,724 B2 | 7/2021 | Pace et al. |
| 11,123,532 B2 | 9/2021 | Pushpala et al. |
| 11,179,068 B2 | 11/2021 | Pace et al. |
| 11,197,985 B2 | 12/2021 | Pushpala et al. |
| 11,272,866 B2 | 3/2022 | Pushpala et al. |
| 11,272,885 B2 | 3/2022 | Pushpala et al. |
| 11,291,390 B2 | 4/2022 | Pushpala et al. |
| 11,331,022 B2 | 5/2022 | Halac et al. |
| 11,359,300 B1 | 6/2022 | Beer et al. |
| 11,406,818 B2 | 8/2022 | Windmiller |
| 11,478,194 B2 | 10/2022 | Windmiller et al. |
| 11,596,332 B2 | 3/2023 | Shults et al. |
| 11,654,270 B2 | 5/2023 | Mansfield, III et al. |
| D988,160 S | 6/2023 | Morelock |
| 11,672,965 B2 | 6/2023 | Mansfield, III et al. |
| 11,697,007 B2 | 7/2023 | Gu et al. |
| D996,999 S | 8/2023 | Morelock |
| 11,819,650 B2 | 11/2023 | Pushpala et al. |
| D1,012,744 S | 1/2024 | Morelock |
| 11,857,344 B2 | 1/2024 | Windmiller et al. |
| 11,865,289 B2 | 1/2024 | Pushpala et al. |
| 11,872,055 B2 | 1/2024 | Tangney et al. |
| D1,013,544 S | 2/2024 | Morelock |
| 11,896,792 B2 | 2/2024 | Pushpala et al. |
| 11,896,793 B2 | 2/2024 | Pushpala et al. |
| 11,903,738 B2 | 2/2024 | Pushpala et al. |
| 11,904,127 B2 | 2/2024 | Mansfield et al. |
| 11,963,796 B1 | 4/2024 | Windmiller et al. |
| 11,986,614 B2 | 5/2024 | Mansfield et al. |
| 11,992,314 B2 | 5/2024 | Hahn et al. |
| 12,011,294 B2 | 6/2024 | Campbell et al. |
| D1,033,641 S | 7/2024 | Morelock |
| D1,035,004 S | 7/2024 | Morelock |
| 12,048,558 B2 | 7/2024 | Kendall et al. |
| D1,038,794 S | 8/2024 | Morelock |
| 12,070,307 B2 | 8/2024 | Ebejer et al. |
| 12,070,313 B2 | 8/2024 | Fuchs et al. |
| 12,109,032 B1 | 10/2024 | Windmiller et al. |
| D1,051,745 S | 11/2024 | Morelock |
| D1,057,153 S | 1/2025 | Morelock |
| 2002/0004640 A1 | 1/2002 | Conn et al. |
| 2002/0020688 A1 | 2/2002 | Sherman et al. |
| 2002/0055704 A1 | 5/2002 | Scott et al. |
| 2002/0072784 A1 | 6/2002 | Sheppard et al. |
| 2002/0105080 A1 | 8/2002 | Speakman |
| 2002/0120186 A1 | 8/2002 | Keimel |
| 2002/0187556 A1 | 12/2002 | Shartle et al. |
| 2003/0068666 A1 | 4/2003 | Zweig |
| 2003/0088166 A1 | 5/2003 | Say et al. |
| 2003/0095582 A1 | 5/2003 | Ackley |
| 2003/0100040 A1 | 5/2003 | Bonnecaze et al. |
| 2003/0104119 A1 | 6/2003 | Wilson et al. |
| 2003/0135158 A1 | 7/2003 | Gonnelli |
| 2003/0199788 A1 | 10/2003 | Erickson et al. |
| 2003/0208167 A1 | 11/2003 | Prausnitz et al. |
| 2003/0225360 A1 | 12/2003 | Eppstein et al. |
| 2003/0235817 A1 | 12/2003 | Bartkowiak et al. |
| 2004/0065158 A1 | 4/2004 | Schrepfer et al. |
| 2004/0082875 A1 | 4/2004 | Donoghue et al. |
| 2004/0138543 A1 | 7/2004 | Russell et al. |
| 2004/0189311 A1 | 9/2004 | Glezer et al. |
| 2004/0220625 A1 | 11/2004 | Silvestri et al. |
| 2005/0036020 A1 | 2/2005 | Li et al. |
| 2005/0101841 A9 | 5/2005 | Kaylor et al. |
| 2005/0137536 A1 | 6/2005 | Gonnelli |
| 2005/0209565 A1 | 9/2005 | Yuzhakov et al. |
| 2005/0267440 A1 | 12/2005 | Herman et al. |
| 2005/0272989 A1 | 12/2005 | Shah et al. |
| 2006/0015061 A1 | 1/2006 | Kuo et al. |
| 2006/0016700 A1 | 1/2006 | Brister et al. |
| 2006/0173259 A1 | 8/2006 | Flaherty et al. |
| 2006/0264716 A1 | 11/2006 | Zander |
| 2006/0281121 A1 | 12/2006 | Unger et al. |
| 2007/0060815 A1 | 3/2007 | Martin et al. |
| 2007/0078445 A1 | 4/2007 | Malloy |
| 2007/0169533 A1 | 7/2007 | Shah et al. |
| 2007/0170054 A2 | 7/2007 | Wilsey |
| 2007/0191733 A1 | 8/2007 | Gianchandani et al. |
| 2007/0213044 A1 | 9/2007 | Steingart et al. |
| 2007/0282246 A1 | 12/2007 | Henley |
| 2008/0009800 A1 | 1/2008 | Nickel |
| 2008/0009801 A1 | 1/2008 | Nickel |
| 2008/0027369 A1 | 1/2008 | Carter et al. |
| 2008/0033269 A1 | 2/2008 | Zhang |
| 2008/0097280 A1 | 4/2008 | Martin et al. |
| 2008/0097352 A1 | 4/2008 | Beck et al. |
| 2008/0119707 A1 | 5/2008 | Stafford |
| 2008/0154107 A1 | 6/2008 | Jina |
| 2008/0156661 A1 | 7/2008 | Cooper et al. |
| 2008/0213461 A1 | 9/2008 | Gill et al. |
| 2008/0221408 A1 | 9/2008 | Hoarau et al. |
| 2008/0234562 A1 | 9/2008 | Jina |
| 2008/0255434 A1 | 10/2008 | Hayter et al. |
| 2008/0275327 A1 | 11/2008 | Faarbaek et al. |
| 2008/0319298 A1* | 12/2008 | Huys ............... G01N 33/48728 600/377 |
| 2009/0043250 A1 | 2/2009 | Gonnelli |
| 2009/0057148 A1 | 3/2009 | Wieder et al. |
| 2009/0062752 A1 | 3/2009 | Gonnelli |
| 2009/0066348 A1 | 3/2009 | Shin et al. |
| 2009/0069651 A1 | 3/2009 | Zimmermann et al. |
| 2009/0069697 A1 | 3/2009 | Frazier et al. |
| 2009/0084678 A1 | 4/2009 | Joshi et al. |
| 2009/0088652 A1 | 4/2009 | Tremblay |
| 2009/0090623 A1 | 4/2009 | Chuang et al. |
| 2009/0099427 A1 | 4/2009 | Jina et al. |
| 2009/0101498 A1 | 4/2009 | Papadimitrakopoulo et al. |
| 2009/0118672 A1 | 5/2009 | Gonnelli et al. |
| 2009/0131778 A1 | 5/2009 | Jina et al. |
| 2009/0143761 A1 | 6/2009 | Cantor et al. |
| 2009/0152598 A1 | 6/2009 | Baek et al. |
| 2009/0191616 A1 | 7/2009 | Lu et al. |
| 2009/0198118 A1 | 8/2009 | Hayter et al. |
| 2009/0218239 A1 | 9/2009 | Gooding et al. |
| 2009/0259118 A1 | 10/2009 | Feldman et al. |
| 2009/0294306 A1 | 12/2009 | Feldman et al. |
| 2010/0006451 A1 | 1/2010 | Gordon et al. |
| 2010/0021637 A1 | 1/2010 | Revol Cavalier et al. |
| 2010/0022416 A1 | 1/2010 | Flemming et al. |
| 2010/0025238 A1 | 2/2010 | Gottlieb et al. |
| 2010/0030045 A1 | 2/2010 | Gottlieb et al. |
| 2010/0049021 A1 | 2/2010 | Jina et al. |
| 2010/0052892 A1 | 3/2010 | Allen et al. |
| 2010/0052897 A1 | 3/2010 | Allen et al. |
| 2010/0052898 A1 | 3/2010 | Allen et al. |
| 2010/0052915 A1 | 3/2010 | Allen et al. |
| 2010/0056873 A1 | 3/2010 | Allen et al. |
| 2010/0108509 A1 | 5/2010 | Curry et al. |
| 2010/0137779 A1 | 6/2010 | Seitz |
| 2010/0160756 A1 | 6/2010 | Petisce et al. |
| 2010/0200538 A1 | 8/2010 | Petisce et al. |
| 2010/0279377 A1 | 11/2010 | Shah et al. |
| 2010/0286803 A1 | 11/2010 | Tillotson et al. |
| 2011/0027127 A1 | 2/2011 | Simpson et al. |
| 2011/0042241 A1 | 2/2011 | Kotsis et al. |

(56) References Cited

U.S. PATENT DOCUMENTS

| | | |
|---|---|---|
| 2011/0077490 A1 | 3/2011 | Simpson et al. |
| 2011/0105871 A1 | 5/2011 | Zimmermann et al. |
| 2011/0140703 A1 | 6/2011 | Chiao et al. |
| 2011/0196216 A1 | 8/2011 | Quarder et al. |
| 2011/0210017 A1 | 9/2011 | Lai et al. |
| 2011/0224515 A1 | 9/2011 | Mir et al. |
| 2011/0230736 A1 | 9/2011 | Tepper et al. |
| 2011/0237925 A1 | 9/2011 | Yue et al. |
| 2011/0247934 A1 | 10/2011 | Wang et al. |
| 2011/0275918 A1 | 11/2011 | Yamashita et al. |
| 2011/0306853 A1 | 12/2011 | Black et al. |
| 2011/0319787 A1 | 12/2011 | Lamoise et al. |
| 2012/0018302 A1 | 1/2012 | Shiraki et al. |
| 2012/0037515 A1 | 2/2012 | Solanki |
| 2012/0067734 A1 | 3/2012 | Wang et al. |
| 2012/0078071 A1 | 3/2012 | Bohm et al. |
| 2012/0123232 A1 | 5/2012 | Najarian et al. |
| 2012/0172692 A1 | 7/2012 | Tamada et al. |
| 2012/0209244 A1 | 8/2012 | Gray |
| 2012/0277629 A1 | 11/2012 | Bernstein et al. |
| 2012/0323097 A9 | 12/2012 | Chowdhury |
| 2013/0053660 A1 | 2/2013 | Shieh |
| 2013/0065257 A1 | 3/2013 | Wang et al. |
| 2013/0135158 A1 | 5/2013 | Faraone et al. |
| 2013/0144131 A1 | 6/2013 | Wang et al. |
| 2013/0158376 A1 | 6/2013 | Hayter et al. |
| 2013/0225956 A1 | 8/2013 | Huang et al. |
| 2013/0281808 A1 | 10/2013 | Shieh |
| 2013/0324820 A1 | 12/2013 | Petillo et al. |
| 2013/0338632 A1* | 12/2013 | Kaplan ............... A61P 43/00 604/173 |
| 2013/0338746 A1 | 12/2013 | Guvanasen et al. |
| 2013/0345597 A1 | 12/2013 | Hagino et al. |
| 2014/0135679 A1 | 5/2014 | Mann et al. |
| 2014/0259652 A1 | 9/2014 | Pushpala et al. |
| 2014/0275897 A1 | 9/2014 | Pushpala et al. |
| 2014/0275899 A1 | 9/2014 | Gottlieb et al. |
| 2014/0275907 A1 | 9/2014 | Feldman et al. |
| 2014/0303471 A1 | 10/2014 | Rajaraman et al. |
| 2014/0336487 A1 | 11/2014 | Wang et al. |
| 2014/0378804 A1 | 12/2014 | Kalvesten et al. |
| 2015/0073238 A1 | 3/2015 | Matsumoto et al. |
| 2015/0126834 A1 | 5/2015 | Wang et al. |
| 2015/0208970 A1 | 7/2015 | Huang |
| 2015/0243851 A1 | 8/2015 | Lee et al. |
| 2015/0276758 A1 | 10/2015 | Addisu |
| 2015/0313527 A1 | 11/2015 | Renlund |
| 2016/0022187 A1 | 1/2016 | Pushpala et al. |
| 2016/0029937 A1 | 2/2016 | Sia et al. |
| 2016/0058342 A1 | 3/2016 | Maiz-Aguinaga et al. |
| 2016/0095541 A1 | 4/2016 | Wang et al. |
| 2016/0095547 A1 | 4/2016 | Wang et al. |
| 2016/0139069 A1 | 5/2016 | Wang |
| 2016/0157764 A1 | 6/2016 | Di Palma et al. |
| 2016/0158514 A1 | 6/2016 | Stoeber et al. |
| 2016/0166184 A1 | 6/2016 | Teng et al. |
| 2016/0213908 A1 | 7/2016 | McAllister et al. |
| 2016/0258945 A1 | 9/2016 | Malima et al. |
| 2016/0270704 A1 | 9/2016 | DeTurk |
| 2016/0296149 A1 | 10/2016 | Polsky et al. |
| 2016/0302687 A1 | 10/2016 | Lee et al. |
| 2016/0370377 A1 | 12/2016 | Ahmad |
| 2017/0003766 A1 | 1/2017 | Budiman |
| 2017/0007813 A1 | 1/2017 | Negi et al. |
| 2017/0035331 A1 | 2/2017 | Paranjape et al. |
| 2017/0055835 A1 | 3/2017 | Scherer et al. |
| 2017/0086713 A1 | 3/2017 | Pushpala et al. |
| 2017/0108459 A1 | 4/2017 | Katsuki et al. |
| 2017/0127989 A1 | 5/2017 | Feldman et al. |
| 2017/0128009 A1 | 5/2017 | Pushpala et al. |
| 2017/0164881 A1 | 6/2017 | Fujita et al. |
| 2017/0251958 A1 | 9/2017 | Pushpala et al. |
| 2017/0251959 A1 | 9/2017 | Feldman et al. |
| 2017/0251960 A1 | 9/2017 | Crouther et al. |
| 2017/0347925 A1 | 12/2017 | Wang et al. |
| 2018/0014787 A1 | 1/2018 | Ganton et al. |
| 2018/0116572 A1 | 5/2018 | Simpson et al. |
| 2018/0140235 A1 | 5/2018 | Pushpala et al. |
| 2018/0279929 A1 | 10/2018 | Huang et al. |
| 2018/0317820 A1 | 11/2018 | Pace et al. |
| 2018/0338712 A1 | 11/2018 | Cass et al. |
| 2018/0340203 A1 | 11/2018 | Holmes et al. |
| 2019/0008425 A1 | 1/2019 | Srinivasan et al. |
| 2019/0022365 A1 | 1/2019 | Chowdhury et al. |
| 2019/0029577 A1 | 1/2019 | Koelker et al. |
| 2019/0076075 A1 | 3/2019 | Miller et al. |
| 2019/0090811 A1 | 3/2019 | Reitz et al. |
| 2019/0091455 A1 | 3/2019 | Reitz et al. |
| 2019/0094169 A1 | 3/2019 | Shah et al. |
| 2019/0101551 A1 | 4/2019 | Plaxco et al. |
| 2019/0110724 A1 | 4/2019 | Kamath et al. |
| 2019/0125223 A1 | 5/2019 | Wang et al. |
| 2019/0167167 A1 | 6/2019 | Mitchell et al. |
| 2019/0170739 A1 | 6/2019 | Garner et al. |
| 2019/0201675 A1 | 7/2019 | Miller et al. |
| 2019/0209095 A1 | 7/2019 | Kamath et al. |
| 2019/0223795 A1 | 7/2019 | Patolsky et al. |
| 2019/0224712 A1 | 7/2019 | Petisce et al. |
| 2019/0231263 A1 | 8/2019 | Ribet et al. |
| 2019/0241926 A1 | 8/2019 | Mckinlay et al. |
| 2019/0261907 A1 | 8/2019 | Brister et al. |
| 2019/0274599 A1 | 9/2019 | Polsky et al. |
| 2019/0274600 A1 | 9/2019 | Pesantez et al. |
| 2019/0298210 A1 | 10/2019 | Bennet et al. |
| 2019/0307379 A1 | 10/2019 | Boock et al. |
| 2019/0309433 A1 | 10/2019 | Sattayasamitsathit et al. |
| 2019/0310219 A1 | 10/2019 | Boock |
| 2019/0357827 A1 | 11/2019 | Li et al. |
| 2020/0000387 A1 | 1/2020 | Gerhardt et al. |
| 2020/0029876 A1 | 1/2020 | Brister et al. |
| 2020/0037938 A1 | 2/2020 | Rong et al. |
| 2020/0101286 A1 | 4/2020 | Windmiller et al. |
| 2020/0121902 A1 | 4/2020 | Pushpala et al. |
| 2020/0178853 A1 | 6/2020 | Pushpala et al. |
| 2020/0187778 A1 | 6/2020 | Brister et al. |
| 2020/0214566 A1 | 7/2020 | Allen et al. |
| 2020/0254240 A1 | 8/2020 | Windmiller et al. |
| 2020/0297997 A1 | 9/2020 | Windmiller et al. |
| 2020/0305771 A1 | 10/2020 | Feldman et al. |
| 2020/0330007 A1 | 10/2020 | Garai et al. |
| 2020/0359949 A1 | 11/2020 | Brauker et al. |
| 2020/0390395 A1 | 12/2020 | Pushpala et al. |
| 2020/0405234 A1 | 12/2020 | Pushpala et al. |
| 2021/0045663 A1 | 2/2021 | Simpson et al. |
| 2021/0045665 A1 | 2/2021 | Simpson et al. |
| 2021/0045666 A1 | 2/2021 | Simpson et al. |
| 2021/0100452 A1 | 4/2021 | Brister et al. |
| 2021/0100504 A1 | 4/2021 | Pushpala et al. |
| 2021/0100505 A1 | 4/2021 | Pushpala et al. |
| 2021/0183508 A1 | 6/2021 | Parker et al. |
| 2021/0187286 A1 | 6/2021 | Windmiller et al. |
| 2021/0190719 A1 | 6/2021 | LaTour et al. |
| 2021/0236057 A1 | 8/2021 | Pushpala et al. |
| 2021/0321942 A1 | 10/2021 | Pushpala et al. |
| 2021/0345916 A1 | 11/2021 | Boock et al. |
| 2021/0353229 A1 | 11/2021 | Pierart et al. |
| 2021/0379370 A1 | 12/2021 | Windmiller et al. |
| 2021/0386338 A1 | 12/2021 | Zhang et al. |
| 2021/0393201 A1 | 12/2021 | Morelock et al. |
| 2022/0031244 A1 | 2/2022 | Windmiller et al. |
| 2022/0047190 A1 | 2/2022 | Taylor et al. |
| 2022/0054813 A1 | 2/2022 | Pushpala et al. |
| 2022/0054814 A1 | 2/2022 | Pushpala et al. |
| 2022/0104773 A1 | 4/2022 | Lee et al. |
| 2022/0151516 A1 | 5/2022 | Wang et al. |
| 2022/0151518 A1 | 5/2022 | Pushpala et al. |
| 2022/0151519 A1 | 5/2022 | Pushpala et al. |
| 2022/0151558 A1 | 5/2022 | Pushpala et al. |
| 2022/0175278 A1 | 6/2022 | Campbell et al. |
| 2022/0175279 A1 | 6/2022 | Pushpala et al. |
| 2022/0175282 A1 | 6/2022 | Hoss et al. |
| 2022/0214300 A1 | 7/2022 | Wang et al. |
| 2022/0225901 A1 | 7/2022 | Chapman et al. |
| 2022/0233107 A1 | 7/2022 | Pushpala et al. |

(56) References Cited

U.S. PATENT DOCUMENTS

| | | |
|---|---|---|
| 2022/0249189 A1 | 8/2022 | Choi et al. |
| 2022/0257181 A1 | 8/2022 | Wang et al. |
| 2022/0298291 A1 | 9/2022 | Shin et al. |
| 2022/0322975 A1 | 10/2022 | Baker et al. |
| 2022/0322977 A1 | 10/2022 | Simpson et al. |
| 2022/0361776 A1 | 11/2022 | Wang et al. |
| 2022/0370011 A1 | 11/2022 | Windmiller et al. |
| 2023/0003725 A1 | 1/2023 | Wang et al. |
| 2023/0012662 A1 | 1/2023 | Tehrani et al. |
| 2023/0074798 A1 | 3/2023 | Tangney et al. |
| 2023/0094419 A1 | 3/2023 | Mansfield, III et al. |
| 2023/0099617 A1 | 3/2023 | Mansfield, III et al. |
| 2023/0137258 A1 | 5/2023 | Windmiller |
| 2023/0190147 A1 | 6/2023 | Campbell et al. |
| 2023/0256220 A1 | 8/2023 | Mansfield, III et al. |
| 2023/0301552 A1 | 9/2023 | Mallires et al. |
| 2023/0310823 A1 | 10/2023 | Mansfield, III et al. |
| 2023/0414102 A1 | 12/2023 | Allen et al. |
| 2024/0008777 A1 | 1/2024 | Fuchs et al. |
| 2024/0081740 A1 | 3/2024 | Windmiller et al. |
| 2024/0164719 A1 | 5/2024 | Campbell et al. |
| 2024/0252115 A1 | 8/2024 | Tangney et al. |
| 2024/0315614 A1 | 9/2024 | Campbell et al. |
| 2024/0341636 A1 | 10/2024 | Yang et al. |
| 2024/0366125 A1 | 11/2024 | Alonso-Soski et al. |
| 2024/0366149 A1 | 11/2024 | Kendall et al. |
| 2024/0382157 A1 | 11/2024 | Windmiller et al. |
| 2024/0408366 A1 | 12/2024 | Mansfield et al. |
| 2025/0000395 A1 | 1/2025 | Brister et al. |
| 2025/0049397 A1 | 2/2025 | Campbell et al. |

FOREIGN PATENT DOCUMENTS

| | | |
|---|---|---|
| CN | 113717955 A | 11/2021 |
| DE | 102015209669 A1 | 12/2016 |
| EP | 1006868 B1 | 6/2004 |
| EP | 1372602 B1 | 4/2007 |
| EP | 1792565 B1 | 10/2008 |
| EP | 1187653 B1 | 3/2010 |
| EP | 2898821 B1 | 12/2017 |
| EP | 3364183 A1 | 8/2018 |
| EP | 3381370 A1 | 10/2018 |
| EP | 3829418 B1 | 11/2024 |
| EP | 3829437 B1 | 11/2024 |
| EP | 4009865 B1 | 11/2024 |
| EP | 4482372 A1 | 1/2025 |
| JP | H0222552 A | 1/1990 |
| JP | H0231741 A | 2/1990 |
| JP | H067324 A | 1/1994 |
| JP | H07275227 A | 10/1995 |
| JP | 2003038464 A | 2/2003 |
| JP | 2003038465 A | 2/2003 |
| JP | 2003111742 A | 4/2003 |
| JP | 2004180773 A | 7/2004 |
| JP | 2005087613 A | 4/2005 |
| JP | 2005525141 A | 8/2005 |
| JP | 2005322591 A | 11/2005 |
| JP | 2006510467 A | 3/2006 |
| JP | 2008512162 A | 4/2008 |
| JP | 2008540013 A | 11/2008 |
| JP | 2008544763 A | 12/2008 |
| JP | 2010523167 A | 7/2010 |
| JP | 2013506847 A | 2/2013 |
| JP | 2013521942 A | 6/2013 |
| JP | 2014533523 A | 12/2014 |
| JP | 2017108763 A | 6/2017 |
| JP | 2019107040 A | 7/2019 |
| JP | 2019526332 A | 9/2019 |
| JP | 2019205852 A | 12/2019 |
| JP | 2020170011 A | 10/2020 |
| JP | 2022501100 A | 1/2022 |
| JP | 2022508575 A | 1/2022 |
| KR | 20160108111 A | 9/2016 |
| WO | WO-0074763 A2 | 12/2000 |
| WO | WO-2006060106 A1 | 6/2006 |
| WO | WO-2006093422 A1 | 9/2006 |
| WO | WO-2006116242 A2 | 11/2006 |
| WO | WO-2007040938 A1 | 4/2007 |
| WO | WO-2009034313 A2 | 3/2009 |
| WO | WO-2009064164 A2 | 5/2009 |
| WO | WO-2009124095 A1 | 10/2009 |
| WO | WO-2010014959 A2 | 2/2010 |
| WO | WO-2010022252 A2 | 2/2010 |
| WO | WO-2010045247 A1 | 4/2010 |
| WO | WO-2010059276 A1 | 5/2010 |
| WO | WO-2010120364 A2 | 10/2010 |
| WO | WO-2011056095 A1 | 5/2011 |
| WO | WO-2012020332 A2 | 2/2012 |
| WO | WO-2012142625 A2 | 10/2012 |
| WO | WO-2013058879 A2 | 4/2013 |
| WO | WO-2014120114 A1 | 8/2014 |
| WO | WO-2015073459 A1 | 5/2015 |
| WO | WO-2016189301 A1 | 12/2016 |
| WO | WO-2017129980 A1 | 8/2017 |
| WO | WO-2017189707 A1 | 11/2017 |
| WO | WO-2018017196 A1 | 1/2018 |
| WO | WO-2018071265 A1 | 4/2018 |
| WO | WO-2018164886 A1 | 9/2018 |
| WO | WO-2018170363 A1 | 9/2018 |
| WO | WO-2019046333 A1 | 3/2019 |
| WO | WO-2019156934 A1 | 8/2019 |
| WO | WO-2019222615 A1 | 11/2019 |
| WO | WO-2019239258 A1 | 12/2019 |
| WO | WO-2020023804 A1 | 1/2020 |
| WO | WO-2020069565 A1 | 4/2020 |
| WO | WO-2020069567 A1 | 4/2020 |
| WO | WO-2020069570 A1 | 4/2020 |
| WO | WO-2020117918 A1 | 6/2020 |
| WO | WO-2021015389 A1 | 1/2021 |
| WO | WO-2021025260 A1 | 2/2021 |
| WO | WO-2021062475 A1 | 4/2021 |
| WO | WO-2021086690 A1 | 5/2021 |
| WO | WO-2021118124 A1 | 6/2021 |
| WO | WO-2021118431 A1 | 6/2021 |
| WO | WO-2021216186 A2 | 10/2021 |
| WO | WO-2021216186 A9 | 12/2021 |
| WO | WO-2022026764 A1 | 2/2022 |
| WO | WO-2022066985 A1 | 3/2022 |
| WO | WO-2022066992 A1 | 3/2022 |
| WO | WO-2022090741 A1 | 5/2022 |
| WO | WO-2022136785 A1 | 6/2022 |
| WO | WO-2022240700 A1 | 11/2022 |
| WO | WO-2023055755 A1 | 4/2023 |
| WO | WO-2023064877 A1 | 4/2023 |
| WO | WO-2023133468 A1 | 7/2023 |
| WO | WO-2023229662 A2 | 11/2023 |
| WO | WO-2024000015 A1 | 1/2024 |
| WO | WO-2024010827 A1 | 1/2024 |
| WO | WO-2024163950 A2 | 8/2024 |
| WO | WO-2024238798 A1 | 11/2024 |

OTHER PUBLICATIONS

Allen et al., "Continuous glucose monitoring counseling improves physical activity behaviors of individuals with type 2 diabetes: A randomized clinical trial" Diabetes Res Clin Pract. Jun. 2008 80(3): 371-379. doi:10.1016/j.diabres.2008.01.006.

American Diabetes Association, "Diabetes and Emotional Health: A Practical Guide for Health Professionals Supporting Adults with Type 1 and Type 2 Diabetes" U.S. Edition (2021), 214 pages.

American Diabetes Association® Press Release (2020). "American Diabetes Association ® Applauds policymakers' Focus on Addressing High Costs of Insulin for Seven Million Americans," 4 pages.

American Diabetes Association Professional Practice Committee, "6. Glycemic Goals and Hypoglycemia: Standards of Care in Diabetes-2024" Diabetes Care Jan. 1, 2024; 47(Suppl 1):S111-S125.

American Diabetes Association Professional Practice Committee, "7. Diabetes Technology: Standards of Medical Care in Diabetes-2022" Diabetes Care Jan. 1, 2022; 45(Suppl 1):S97-S112.

Bantle, J.P. et al. (1997). "Glucose measurement in patients with diabetes mellitus with dermal interstitial fluid," J. Lab. Clin. Med. 130:436-441.

(56) References Cited

OTHER PUBLICATIONS

Barrett et al., "Risk for Newly Diagnosed Diabetes 30 Days After SARS-COV-2 Infection Among Persons Aged 18 Years—United States, Mar. 1, 2020-Jun. 28, 2021" MMWR Morb Mortal Wkly Rep. Jan. 14, 2020; 71(2):59-65. doi: 10.15585/mmwr.mm7102e2.
Beckles, G.L. et al. (2016). "Disparities in the prevalence of diagnosed diabetes—United States, 1999-2002 and 2011-2014," MMWR 65:1265-1269.
Brown, "Design of Electronics for Wearable Electrochemical Sensors" University of California, San Diego, Master's Thesis (2019) 48 pages.
Cao, J. et al. (2017). "Validation of capillary blood analysis and capillary testing mode on the epoc Point of Care system," Pract. Lab. Med. 9:24-27.
Castle, J.R. et al. (2012). "The accuracy benefit of multiple amperometric glucose sensors in people with type 1 diabetes," Diabetes Care 35:706-710.
Centers for Disease Control, "National Diabetes Statistics Report 2020 Estimates of Diabetes and Its Burden in the United States" (2020) 32 pages.
Centers for Disease Control, "National Diabetes Statistics Report" May 2024, 16 pages.
Chang, H. et al. (2017). "A swellable microneedle patch to rapidly extract skin interstitial fluid for timely metabolic analysis," Adv. Mater. 29:1702243. 8 pages.
Chen et al., "Electrochemically Mediated Electrodeposition/Electropolymerization To Yield a Glucose Microbiosensor with Improved Characteristics" Anal. Chem. (2002) 74:368-372.
Diabetes Care (2021). "7. Diabetes Technology: Standards of Medical Care in Diabetes—2021," Diabetes Care 44(Supplement 1):S85-S99.
Diabetes Control and Complications Trial Research Group, "The effect of intensive treatment of diabetes on the development and progression of long-term complications in insulin-dependent diabetes mellitus" N Engl J Med Sep. 30 1993; 329(14):977-986.
Donnelly, R.F et al. (2007). "Microstructured Devices for Transdermal Drug Delivery and Minimally-Invasive Patient Monitoring," Recent Patents on Drug Delivery & Formulation 1:195-200.
Dunkin et al., "Scarring occurs at a critical depth of skin injury: precise measurement in a graduated dermal scratch in human volunteers" Plast Reconstr Surg. May 2007; 119(6):1722-1732. doi: 10.1097/01.prs.0000258829.07399.f0.
Ehrhardt et al., "Behavior Modification in Prediabetes and Diabetes: Potential Use of Real-Time Continuous Glucose Monitoring" Journal of Diabetes Science and Technology Mar. 2019; 13(2):271-275.
Ehrhardt et al., "Continuous Glucose Monitoring As a Behavior Modification Tool" Clin Diabetes. Apr. 2020; 38(2):126-131. doi: 10.2337/cd19-0037.
Ehrhardt et al., "The Effect of Real-Time Continuous Glucose Monitoring on Glycemic Control in Patients with Type 2 Diabetes Mellitus" Journal of Diabetes Science and Technology May 2011; 5(3):668-675.
Elsayed et al., "2. Classification and Diagnosis of Diabetes: Standards of Care in Diabetes-2023" Diabetes Care Jan. 1, 2023; 46(Suppl 1):S19-S40.
Extended European Search Report for European Application No. 23218205.5 dated Jun. 11, 2024, 7 pages.
Extended European Search Report for European Application No. EP20898007.8 dated Nov. 29, 2023, 9 pages.
Extended European Search Report for European Application No. EP21837561.6 dated Jun. 21, 2024, 7 pages.
Extended European Search Report mailed on Mar. 30, 2023, for European Application No. EP20881425.1, 8 pages.
Extended European Search Report mailed on May 8, 2015, for EP Application No. 12842020.5, filed on Aug. 31, 2012, 7 pages.
Extended European Search Report mailed on Oct. 27, 2022, for EP Application No. 21850331.6, filed on Jul. 29, 2021, 8 pages.
Fang, M. et al. (2021). "Trends in Diabetes Treatment and Control in U.S. Adults, 1999-2018," N. Engl. J. Med. 384:2219-2228.

Final Office Action for U.S. Appl. No. 18/527,128 mailed Sep. 6, 2024, 19 pages.
Final Office Action for U.S. Appl. No. 18/630,936 mailed Sep. 20, 2024, 16 pages.
Final Office Action mailed on Aug. 15, 2022, for U.S. Appl. No. 16/051,398, filed Jul. 31, 2018, 15 pages.
Final Office Action mailed on Aug. 19, 2016, for U.S. Appl. No. 14/965,755, filed Dec. 10, 2015, 17 pages.
Final Office Action mailed on Aug. 29, 2023, for U.S. Appl. No. 18/086,543, filed Dec. 21, 2022, 17 pages.
Final Office Action mailed on Dec. 7, 2020, for U.S. Appl. No. 15/961,793, filed Apr. 24, 2018, 13 pages.
Final Office Action mailed on Feb. 1, 2024, for U.S. Appl. No. 17/073,331, filed Oct. 17, 2020, 12 pages.
Final Office Action mailed on Feb. 8, 2024, for U.S. Appl. No. 16/051,398, filed Jul. 31, 2018, 15 pages.
Final Office Action mailed on Jul. 15, 2022, for U.S. Appl. No. 17/650,056, filed Feb. 4, 2022, 25 pages.
Final Office Action mailed on Jun. 9, 2021, for U.S. Appl. No. 16/169,939, filed Oct. 24, 2018, 24 pages.
Final Office Action mailed on Mar. 15, 2024, for U.S. Appl. No. 17/367,274, filed Jul. 2, 2021, 33 pages.
Final Office Action mailed on May 18, 2018, for U.S. Appl. No. 15/687,145, filed Aug. 25, 2017, 23 pages.
Final Office Action mailed on May 21, 2021, for U.S. Appl. No. 16/051,398, filed Jul. 31, 2018, 11 pages.
Final Office Action mailed on May 9, 2022, for U.S. Appl. No. 17/389,153, filed Jul. 29, 2021, 17 pages.
Final Office Action mailed on Nov. 27, 2023, for U.S. Appl. No. 17/389,156, filed Jul. 29, 2021, 29 pages.
Final Office Action mailed on Nov. 28, 2016, for U.S. Appl. No. 14/342,536, filed Jul. 30, 2014, 34 pages.
Final Office Action mailed on Oct. 27, 2022, for U.S. Appl. No. 15/913,709, filed Mar. 6, 2018, 21 pages.
Final Office Action mailed on Sep. 23, 2021, for U.S. Appl. No. 15/913,709, filed Mar. 6, 2018, 17 pages.
Final Office Action mailed on Sep. 7, 2023, for U.S. Appl. No. 17/650,056, filed Feb. 4, 2022, 29 pages.
Fonda et al., "The Cost-Effectiveness of Real-Time Continuous Glucose Monitoring (RT-CGM) in Type 2 Diabetes" Journal of Diabetes Science and Technology (2016) 10(4):898-904.
French, D.P. et al. (2008). "Original Article: Psychological Care Self-monitoring of blood glucose changed non-insulin-treated Type 2 diabetes patients' beliefs about diabetes and self-monitoring in a randomized trial," Diav. Med. 25:1218-1228.
Gittard, S.D. et al. (2009). "Fabrication of Polymer Microneedles Using a Two-Photon Polymerization and Micromolding Process," J. Diabetes Sci. Technol. 3:304- 311.
Grady, M. et al. (2017). "Examining the Impact of a Novel Blood Glucose Monitor with Color Range Indicator on Decision-Making in Patients With Type 1 and Type 2 Diabetes and its Association With Patient Numeracy Level," JMIR Diabetes 2:e24. 11 pages.
Grady, M. et al. (2018). "Use of Blood Glucose Meters Featuring Color Range Indicators Improves Glycemic Control in Patients with Diabetes in Comparison to Blood Glucose Meters Without Color (ACCENTS Study)," J. Diab. Sci. Tech. 12:1211-1219.
Groenendaal, W. et al. (2008). "Modeling Glucose and Water Dynamics in Human Skin," Diab. Tech. Therap. 10:283-293.
Han et al., "The End of the Road for the YSI 2300 Analyzer: Where Do We Go Now?" Journal of Diabetes Science and Technology (2020) 14(3):595-600.
Han et al., "The YSI 2300 Analyzer Replacement Meeting Report" Journal of Diabetes Science and Technology (2020) 14(3):679-686.
International Search Report and Written Opinion for Application No. PCT/US2022/028196, mailed on Aug. 29, 2022, 8 pages.
International Search Report and Written Opinion for PCT Application No. PCT/US2020/064700, mail date Mar. 9, 2021, 11 pages.
International Search Report and Written Opinion for PCT Application No. PCT/US2024/014324 mailed Sep. 20, 2024, 22 pages.
International Search Report and Written Opinion mailed on Feb. 6, 2024, for International Application No. PCT/US2022/078819, filed on Oct. 27, 2022, 13 pages.

(56) References Cited

OTHER PUBLICATIONS

International Search Report mailed on Dec. 30, 2021, for PCT Application No. PCT/US2021/043786, filed on Jul. 29, 2021, 7 pages.
International Search Report mailed on Feb. 4, 2021, for PCT Application No. PCT/US2020/056517, filed on Oct. 20, 2020,2 pages.
International Search Report mailed on Jun. 27, 2013, for PCT Application No. PCT/US2012/053544, filed on Aug. 31, 2012, 4 pages.
International Search Report mailed on Sep. 10, 2020, for PCT Application No. PCT/US2020/037379, filed on Jun. 12, 2020, 2 pages.
International Search Report mailed on Sep. 30, 2021, for PCT Application No. PCT/US2021/040385, filed on Jul. 2, 2021, 2 pages.
Invitation to pay additional fees for International Application No. PCT/US2024/014324, dated Jul. 30, 2024, 16 pages.
Jeon, G. et al. (2011). "Electrically Actuatable Smart Nanoporous Membrane for Pulsatile Drug Release," Nano Lett. 11:1284-1288.
Jina, A. et al. (2014). "Design, development, and evaluation of a novel microneedle array-based continuous glucose monitor," J. Diabetes Sci. Technol. 8:483-487.
Juvenile Diabetes Research Foundation Continuous Glucose Monitoring Study Group (2008). "Continuous Glucose Monitoring and Intensive Treatment of Type 1 Diabetes," N. Engl. Med. 359:1464-1476.
Karter, A.J. et al. (2021). "Association of Real-time Continuous Glucose Monitoring With Glycemic Control and Acute Metabolic Events Among Patients With Insulin-Treated Diabetes," JAMA 325:2273-2284.
Lhernould, M.S et al. (2015). "Review of Patents for Microneedle Application Devices Allowing Fluid Injections Through the Skin," Recent Patents on Drug Delivery & Formulation 9:146-157.
Malitesta et al. (1990). "Glucose fast-response amperometric sensor based on glucose oxidase immobilized in an electropolymerized poly(o-phenylenediamine) film," Anal. Chem. 62:2735-2740.
Martens, T. et al. (2021). "Effect of Continuous Glucose Monitoring on Glycemic Control in Patients with Type 2 Diabetes Treated with Basal Insulin A Randomized Clinical Trial," JAMA 325:2262-2272.
McClatchey, P.M et al. (2019). "Fibrotic Encapsulation Is the Dominant Source of Continuous Glucose Monitor Delays," Diabetes 68:1892-1901.
Mendes-Soares et al., "Assessment of a Personalized Approach to Predicting Postprandial Glycemic Responses to Food Among Individuals Without Diabetes" JAMA Network Open Feb. 1, 2019; 2(2):e188102. 13 pages.
Miller et al., "Hypoglycemia in patients with type 2 diabetes mellitus" Arch Intern Med Jul. 9, 2001; 161(13):1653-1659.
Miller, P.R. et al. (2011). "Integrated carbon fiber electrodes within hollow polymer microneedles for transdermal electrochemical sensing," BioMicrofluidics 5(1):013415. 14 pages.
Mohan, A.M. (2017). "Continuous minimally-invasive alcohol monitoring using microneedle sensor arrays," Biosensors and Bioelectronics 91:574-579.
Neerken, S. et al. (2004). "Characterization of age-related effects in human skin: A comparative study that applies confocal laser scanning microscopy and optical coherence tomography," J. Biomed. Optics 9:274-281.
Newton et al., "Diabetic ketoacidosis in type 1 and type 2 diabetes mellitus: clinical and biochemical differences" Arch Intern Med Sep. 27, 2004; 164(17):1925-1931.
Non-Final Office Action for U.S. Appl. No. 17/073,331 mailed Aug. 28, 2024, 13 pages.
Non-Final Office Action for U.S. Appl. No. 17/389,156 dated Apr. 16, 2024, 28 pages.
Non-Final Office Action for U.S. Appl. No. 18/630,936 mailed Jun. 13, 2024, 19 pages.
Non-Final Office Action mailed on Apr. 13, 2020, for U.S. Appl. No. 15/961,793, filed Apr. 24, 2018, 13 pages.
Non-Final Office Action mailed on Apr. 6, 2017, for U.S. Appl. No. 14/342,536, filed Jul. 30, 2014, 32 pages.
Non-Final Office Action mailed on Apr. 8, 2022, for U.S. Appl. No. 17/650,056, filed Feb. 4, 2022, 14 pages.
Non-Final Office Action mailed on Dec. 13, 2023, for U.S. Appl. No. 18/086,543, filed Dec. 21, 2022, 16 pages.
Non-Final Office Action mailed on Dec. 21, 2022, for U.S. Appl. No. 16/051,398, filed Jul. 31, 2018, 12 pages.
Non-Final Office Action mailed on Feb. 16, 2023 for U.S. Appl. No. 17/738,990, 9 pages.
Non-Final Office Action mailed on Jan. 19, 2018, for U.S. Appl. No. 14/843,926, filed Sep. 2, 2015, 11 pages.
Non-Final Office Action mailed on Jan. 26, 2024, for U.S. Appl. No. 15/913,709, filed Mar. 6, 2018, 20 pages.
Non-Final Office Action mailed on Jan. 27, 2023, for U.S. Appl. No. 17/971,415, filed Oct. 21, 2022, 15 pages.
Non-Final Office Action mailed on Jul. 30, 2024, for U.S. Appl. No. 17/650,056, filed Feb. 4, 2022, 32 pages.
Non-Final Office Action mailed on Jun. 2, 2023, for U.S. Appl. No. 17/367,274, filed Jul. 2, 2021, 27 pages.
Non-Final Office Action mailed on Jun. 20, 2023, for U.S. Appl. No. 17/073,331, filed Oct. 17, 2020, 10 pages.
Non-Final Office Action mailed on Mar. 10, 2016, for U.S. Appl. No. 14/965,755, filed Dec. 10, 2015, 15 pages.
Non-Final Office Action mailed on Mar. 29, 2023, for U.S. Appl. No. 17/650,056, filed Feb. 4, 2022, 27 pages.
Non-Final Office Action mailed on Mar. 30, 2016, for U.S. Appl. No. 14/342,536, filed Jul. 30, 2014, 31 pages.
Non-Final Office Action mailed on Mar. 9, 2017, for U.S. Appl. No. 14/965,755, filed Dec. 10, 2015, 17 pages.
Non-Final Office Action mailed on Mar. 9, 2023 for U.S. Appl. No. 17/389,156, filed Jul. 29, 2021, 24 pages.
Non-Final Office Action mailed on May 13, 2022, for U.S. Appl. No. 15/913,709, filed Mar. 6, 2018, 20 pages.
Non-Final Office Action mailed on May 2, 2023, for U.S. Appl. No. 15/913,709, filed Mar. 6, 2018, 18 pages.
Non-Final Office Action mailed on May 24, 2023, for U.S. Appl. No. 18/086,543, filed Dec. 21, 2022, 19 pages.
Non-Final Office Action mailed on May 24, 2024, for U.S. Appl. No. 18/527,128, filed Dec. 1, 2023, 17 pages.
Non-Final Office Action mailed on Nov. 1, 2017, for U.S. Appl. No. 15/687,145, filed on Aug. 25, 2017, 19 pages.
Non-Final Office Action mailed on Nov. 26, 2021, for U.S. Appl. No. 16/051,398, filed Jul. 31, 2018, 15 pages.
Non-Final Office Action mailed on Nov. 29, 2021, for U.S. Appl. No. 17/389,153, filed Jul. 29, 2021, 14 pages.
Non-Final Office Action mailed on Nov. 4, 2021, for U.S. Appl. No. 16/169,939, filed Oct. 24, 2018, 20 pages.
Non-Final Office Action mailed on Oct. 16, 2020, for U.S. Appl. No. 16/051,398, filed Jul. 31, 2018, 13 pages.
Non-Final Office Action mailed on Sep. 15, 2023, for U.S. Appl. No. 16/051,398, filed Jul. 31, 2018, 12 pages.
Non-Final Office Action mailed on Sep. 16, 2020, for U.S. Appl. No. 15/913,709, filed Mar. 6, 2018, 15 pages.
Non-Final Office Action mailed on Sep. 3, 2020, for U.S. Appl. No. 16/169,939, filed Oct. 24, 2018, 19 pages.
Notice of Allowance (Corrected) mailed on Apr. 19, 2024, for U.S. Appl. No. 18/086,543, filed Dec. 21, 2022, 4 pages.
Notice of Allowance (Corrected) mailed on Jan. 25, 2024, for U.S. Appl. No. 17/349,234, filed Jun. 16, 2021, 4 pages.
Notice of Allowance (Corrected) mailed on Mar. 18, 2024, for U.S. Appl. No. 17/349,234, filed Jun. 16, 2021, 9 pages.
Notice of Allowance for U.S. Appl. No. 17/389,156 mailed Sep. 25, 2024, 12 pages.
Notice of Allowance mailed on Apr. 10, 2024, for U.S. Appl. No. 18/086,543, filed Dec. 21, 2022, 10 pages.
Notice of Allowance mailed on Aug. 24, 2018, for U.S. Appl. No. 15/687,145, filed Aug. 25, 2017, 7 pages.
Notice of Allowance mailed on Dec. 20, 2023, for U.S. Appl. No. 17/349,234, filed Jun. 16, 2021, 13 pages.
Notice of Allowance mailed on Feb. 13, 2018, for U.S. Appl. No. 14/843,926, filed Sep. 2, 2015, 8 pages.

(56) References Cited

OTHER PUBLICATIONS

Notice of Allowance mailed on Jul. 12, 2017, for U.S. Appl. No. 14/342,536, filed Jul. 30, 2014, 14 pages.
Notice of Allowance mailed on Jul. 6, 2017, for U.S. Appl. No. 14/965,755, filed Dec. 10, 2015, 12 pages.
Notice of Allowance mailed on Jun. 11, 2024, for U.S. Appl. No. 15/913,709, filed Mar. 6, 2018, 9 pages.
Notice of Allowance mailed on Jun. 12, 2023, for U.S. Appl. No. 17/738,990, filed May 6, 2022, 7 pages.
Notice of Allowance mailed on Jun. 12, 2023, for U.S. Appl. No. 17/971,415, filed Oct. 21, 2022, 14 pages.
Notice of Allowance mailed on Mar. 21, 2024, for U.S. Appl. No. 18/086,543, filed Dec. 21, 2022, 6 pages.
Notice of Allowance mailed on Mar. 4, 2024, for U.S. Appl. No. 18/086,543, filed Dec. 21, 2022, 10 pages.
Notice of Allowance mailed on May 25, 2021, for U.S. Appl. No. 15/961,793, filed Apr. 24, 2018, 11 pages.
Notice of Allowance mailed on Sep. 12, 2022, for U.S. Appl. No. 17/389,153, filed on Jul. 29, 2021, 8 pages.
Notice of Allowance mailed on Sep. 25, 2023, for U.S. Appl. No. 17/971,415, filed Oct. 21, 2022, 8 pages.
Notice of Allowance mailed on Sep. 26, 2023, for U.S. Appl. No. 17/738,990, filed May 6, 2022, 7 pages.
Office Action and Swedish Search Report mailed on Oct. 17, 2023, for SE Application No. 2251496-2, 8 pages.
Polonsky, W.H. et al. (2011). "A survey of blood glucose monitoring in patients with type 2 diabetes: Are recommendations from health care professionals being followed?" Curr. Med. Res. & Opinion 27:31-37.
Rigla, M. et al. (2018). "Human Subcutaneous Tissue Response to Glucose Sensors: Macrophages Accumulation Impact on Sensor Accuracy," Diabetes Technology & Therapeutics 20:296-302.
Sachdeva, V. et al. (2011). "Microneedles and their applications," Recent Patents on Drug Delivery & Formulation 5:95-132.
Segel et al., "Hypoglycemia-associated autonomic failure in advanced type 2 diabetes" Diabetes Mar. 2002; 51(3):724-733.
Sharifi et al., "Redundancy in Glucose Sensing: Enhanced Accuracy and Reliability of an Electrochemical Redundant Sensor for Continuous Glucose Monitoring" Journal of Diabetes Science and Technology (2016) 10(3):669-678.
Sheikh, Z. et al. (2015). "Macrophages, Foreign Body Giant Cells and Their Response to Implantable Biomaterials," Materials 8:5671-5701.
Shi, T. et al. (2016). "Modeling and Measurement of Correlation between Blood and Interstitial Glucose Changes," J. Diab. Res. vol. 2016, 9 pages.
Shivers et al., "Turn it off !: diabetes device alarm fatigue considerations for the present and the future" J Diabetes Sci Technol May 1, 2013; 7(3):789-794.
Singh, T.R.R. et al. (2010). "Microporation techniques for enhanced delivery of therapeutic agents," Recent Patents on Drug Delivery & Formulation 4:1-17.
Supplementary European Search Report mailed on Oct. 9, 2023, for EP Application No. 22808101.4, 4 pages.
Swedish Search Report mailed on Feb. 3, 2023 for SE Application No. 2350067-1, 7 pages.
Tanenbaum et al., "Diabetes Device Use in Adults With Type 1 Diabetes: Barriers to Uptake and Potential Intervention Targets" Diabetes Care Feb. 2017; 40(2):181-187.
Texas Instruments (Sep. 2007). Data sheet for a LMP2234 quad micropower, 1.6V, precision, operational amplifier with CMOS input, Sep. 2007, revised Mar. 2013. 31 total pages.
Turner et al., "Intensive blood-glucose control with sulphonylureas or insulin compared with conventional treatment and risk of complications in patients with type 2 diabetes (UKPDS 33)" The Lancet Sep. 1998; 352(9131):837-853.
UK Prospective Diabetes Study (UKPDS) Group, "Intensive blood-glucose control with sulphonylureas or insulin compared with conventional treatment and risk of complications in patients with type 2 diabetes (UKPDS 33)" Lancet Sep. 12, 1998; 352(9131):837-853.
Vigersky et al., "Short- and Long-Term Effects of Real-Time Continuous Glucose Monitoring in Patients with Type 2 Diabetes" Diabetes Care Jan. 2012; 35:32-38.
Ward et al., "A Wired-Based Dual-Analyte Sensor for Glucose and Lactate: In Vitro and In Vivo Evaluation" Diabetes Technology and Therapeutics Jun. 2004; 6(3):389-401.
Windmiller, J.R. (2012). "Molecular scale biocomputing: An enzyme logic approach," University of California, San Diego, A dissertation submitted in partial satisfaction of the requirements for the degree Doctor of Philosophy in Electrical Engineering (Photonics), 78 total pages.
Windmiller, J.R. et al. (2011). "Bicomponent microneedle array biosensor for minimally-invasive glutamate monitoring," Electroanalysis 23:2302-2309.
Windmiller, J.R. et al. (2011). "Microneedle array-based carbon paste amperometric sensors and biosensors," Analyst 136:1846-1851.
Wolicki et al., "Epidemiology and Prevention of Vaccine-Preventable Diseases: Chapter 6: Vaccine Administration" Centers for Disease Control and Prevention (2021) 17 pages.
World Health Organization, "Diabetes", Sep. 16, 2022, 5 pages.
Written Opinion of the International Search Authority mailed on Sep. 10, 2020, for PCT Application No. PCT/US2020/037379, filed on Jun. 12, 2020, 4 pages.
Written Opinion of the International Searching Authority mailed on Dec. 30, 2021, for PCT Application No. PCT/US2021/043786, filed on Jul. 29, 2021, 10 pages.
Written Opinion of the International Searching Authority mailed on Feb. 4, 2021, for PCT Application No. PCT/US2020/056517, filed on Oct. 20, 2020, 5 pages.
Written Opinion of the International Searching Authority mailed on Jun. 27, 2013, for PCT Application No. PCT/US2012/053544, filed on Aug. 31, 2012, 15 pages.
Written Opinion of the International Searching Authority mailed on Sep. 30, 2021, for PCT Application No. PCT/US2021/040385, filed on Jul. 2, 2021, 5 pages.
Yoon, Y. et al. (2013). "Fabrication of a Microneedle/CNT Hierarchical Micro/Nano Surface Electrochemical Sensor and Its In-Vitro Glucose Sensing Characterization," Sensors 13:16672-16681.
Young et al., "Glucose Self-monitoring in Non-Insulin-Treated Patients With Type 2 Diabetes in Primary Care Settings: A Randomized Trial" JAMA Intern Med. Jul. 2017; 177(7):920-929.
Battelino et al., "Continuous glucose monitoring and metrics for clinical trials: an international consensus statement" Lancet Diabetes Endocrinol (2023) 11:42-57.
Clutter et al., "Epinephrine plasma metabolic clearance rates and physiologic thresholds for metabolic and hemodynamic actions in man" J Clin Invest. (1980) 66(1):94-101.
Czupryniak et al., "Ambulatory Glucose Profile (AGP) Report in Daily Care of Patients with Diabetes: Practical Tips and Recommendations" Diabetes Ther (2022) 13:811-821.
Donnelly et al., "Microneedle Arrays Allow Lower Microbial Penetration Than Hypodermic Needles In Vitro" Pharmaceutical Research (2009) 26(11):2513-2522.
Fayfman et al., "Management of Hyperglycemic Crises: Diabetic ketoacidosis and hyperglycemic hyperosmolar state" Med Clin North Am. May 2017; 101(3):587-606.
Final Office Action for U.S. Appl. No. 17/073,331 mailed Dec. 17, 2024, 13 pages.
Final Office Action for U.S. Appl. No. 17/650,056 mailed on Feb. 14, 2025, 34 pages.
Gao et al., "Simultaneous detection of glucose, uric acid and cholesterol using flexible microneedle electrode array-based biosensor and multi-channel portable electrochemical analyzer" Sensors and Actuators B: Chemical (2019) 287:102-110.
Ghimire et al., "Ketoacidosis" StatPearls Publishing, Jan. 2024, NCBI Bookshelf, 8 pages.
Heinemann, "Interferences With CGM Systems: Practical Relevance?" Journal of Diabetes Science and Technology (2022) vol. 16(2) 271-274.

(56) References Cited

OTHER PUBLICATIONS

Henry et al. "Microfabricated microneedles: a novel approach to transdermal drug delivery." Journal of pharmaceutical sciences. Aug. 1, 1998;87(8):922-925.
Maahs et al., "Effect of Acetaminophen on CGM Glucose in an Outpatient Setting" Diabetes Care (2015) 38:e158-e159.
Nguyen et al., "Human studies with microneedles for evaluation of their efficacy and safety" Expert Opinion on Drug Delivery (2018) 15:3, 235-245.
Non-Final Office Action for U.S. Appl. No. 16/051,398 mailed Feb. 20, 2025, 13 pages.
Non-Final Office Action for U.S. Appl. No. 17/389,156 mailed Jan. 22, 2025, 17 pages.
Non-Final Office Action for U.S. Appl. No. 18/431,808 mailed Nov. 27, 2024, 16 pages.
Non-Final Office Action for U.S. Appl. No. 18/630,936 mailed on Dec. 12, 2024, 18 pages.
Non-Final Office Action for U.S. Appl. No. 18/926,029 mailed on Dec. 12, 2024, 10 pages.
Notice of Allowance for U.S. Appl. No. 17/389,156 mailed Dec. 27, 2024, 6 pages.
Notice of Allowance for U.S. Appl. No. 17/389,156 mailed Nov. 20, 2024, 5 pages.
Notice of Allowance for U.S. Appl. No. 18/431,808 mailed Feb. 20, 2025, 7 pages.
Notice of Allowance for U.S. Appl. No. 18/527,128 mailed Feb. 26, 2025, 9 pages.
Notice of Allowance for U.S. Appl. No. 18/926,029 mailed Mar. 5, 2025, 8 pages.
Ohashi et al., "Analgesic Effect of Acetaminophen: A Review of Known and Novel Mechanisms of Action" Front Pharmacol. Nov. 30, 2020;11:580289, 6 pages.
Prausnitz, "Engineering Microneedle Patches for Vaccination and Drug Delivery to Skin" Annu. Rev. Chem. Biomol. Eng. (2017) 8:177-200.
Samant et al., "Mechanisms of sampling interstitial fluid from skin using a microneedle patch," Proc. Natl Acad. Sci. U.S.A. (2018) 115(8):4583-4588.
Vicente-Perez et al., "Repeat application of microneedles does not alter skin appearance or barrier function and causes No. measurable disturbance of serum biomarkers of infection, inflammation or immunity in mice in vivo" European Journal of Pharmaceutics and Biopharmaceutics (2017) 117:400-407.
Yue et al., "Evaluation of a 12-Hour Sustained-Release Acetaminophen (Paracetamol) Formulation: A Randomized, 3-Way Crossover Pharmacokinetic and Safety Study in Healthy Volunteers" Clinical Pharmacology in Drug Development (2018) 7(1) 95-101.

\* cited by examiner

METHODS FOR ACHIEVING AN ISOLATED ELECTRICAL INTERFACE BETWEEN AN ANTERIOR SURFACE OF A MICRONEEDLE STRUCTURE AND A POSTERIOR SURFACE OF A SUPPORT STRUCTURE

CROSS REFERENCE TO RELATED APPLICATION APPLICATIONS

The present Application is a continuation of U.S. patent application Ser. No. 15/913,709 filed on Mar. 6, 2018, which claims priority to U.S. Provisional Patent Application No. 62/470,204 filed on Mar. 11, 2017, each of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to methods for manufacturing microneedle structures.

Description of the Related Art

Microneedle-based electrochemical biosensor devices have witnessed increased development activity in recent years and rely on the interaction between an electrical signal and a biological analyte. However, to serve useful purposes, these devices must be fabricated using design topologies that are compatible with existing packaging methods. In this vein, current chip-scale implementations of microneedle biosensors (and drug delivery actuators, for that matter) require wire-bonding or flip-chip methods of establishing electrical contact with the active sensing (or transducing) element located on or within the microneedle structure. In spite of this approach, wire bonding and flip-chip methods are not compatible with useful embodiments of sensing/therapeutic capabilities as these modalities would serve to obstruct the microneedle surface and prevent reliable penetration of the stratum corneum. The current methodology allows for an alternative to wire-bonding and flip-chip methods of electrical interface by means of circumscribing electrically-conductive microneedles with an insulating barrier to facilitate a spatially-defined region that can be probed on the posterior surface of the substrate on which the microneedle elements are located.

Microneedle-based electrochemical biosensors represent a promising avenue towards the minimally-invasive quantification of a number of relevant analytes in the physiological fluid, such as interstitial fluid, blood, serum, and plasma. In such devices, an electrical signal is applied to the surface of a microneedle, which concomitantly instigates an electrochemical reaction to either oxidize or reduce an analyte or product of the analyte and a surface-immobilized intermediary. The resultant magnitude of potential or current arising from the redox reaction, which reflects the concentration of analyte in the physiological medium, is then routed to an external integrated circuit, module, or self-contained device for interpretation. In order to facilitate electrical interface between the skin-penetrating regions of the microneedle and a suitable location where the redox signal can be probed, conductive traces are spatially defined from the sensing region located on the microneedle surface to a pad located on the extremities of the substrate upon which the microneedles are secured. However, current chip-scale packaging techniques such as wire-bonding mandate that electrical leads be soldered on the same surface in which the microneedles are located; this can interfere with the insertion of the said microneedles due to increased standoff. On the other hand, flip-chip techniques mandate that the substrate be 'flipped' to facilitate electrical interface, which thereby serves to orient the microneedle structure(s) away from the intended application site and into the interior of the package itself. In order to maintain compatibility with existent packaging methods, the fabrication of said microneedle devices mandates that a spatially-defined conductive region be realized between the sensing surface located on the microneedle structure and the posterior surface of the substrate that the said microneedle is located. In accordance with current practice, this has proven difficult to remedy as the spatial definition of a suitable conduit providing electrical communication between two opposing sides of the substrate required modifications to the fabrication methodology.

Prior art solutions have been concerned with patterned, planar conductive traces routing the electrical signal from the microneedle surface to a spatially defined region (pad) suitable for probing/wire-bonding to facilitate implementation in an integrated circuit-style package. The said pad is located on the same surface as the microneedle structure, which, when attached to an external circuit with bonding wire, will cause increased standoff and prevent the microneedle structure from fully inserting into the viable epidermis or dermis. The trace is not routed through the substrate supporting said microneedle(s) and occupies the same surface as the microneedle.

U.S. Pat. No. 6,551,849 for a Method For Fabricating Arrays Of Micro-Needles discloses an array of microneedles is created by forming an array pattern on the upper surface of a silicon wafer and etching through openings in the pattern to define micro-needle sized cavities having a desired depth. The mold thus formed may be filled with electrically conductive material, after which a desired fraction of the silicon wafer bulk is removed from the bottom-up by etching, to expose an array of projecting micro-needles. The mold may instead be filled with a flexible material to form a substrate useful in gene cell probing. An array of hollow micro-needles may be formed by coating the lower wafer surface with SiN, and etching through pattern openings in the upper surface down to the SiN layer, and then conformally coating the upper surface with thermal silicon dioxide. The SiN layer is then stripped away and a desired fraction of the bulk of the wafer removed from the bottom-up to expose an array of projecting hollow micro-needles.

U.S. Patent Publication Number 20140303471 for Non-Invasive Segmentable Three-Dimensional Microelectrode Array Patch For Neurophysiological Diagnostics And Therapeutic Stimulation discloses implementations disclosed herein provide for a microneedle electrode system comprising a microneedle electrode patch connected to external electronics. The microneedle electrode patch comprises a first flexible substrate having a plurality of conductive pads disposed thereon, a plurality of three-dimensional, individually addressable microneedle electrode arrays where each array has a plurality of microneedles extending from an upper surface thereof and a lower surface adapted to contact a corresponding one of the plurality of conductive pads disposed on the first substrate, and a second flexible substrate having a plurality of openings defined therein dimensioned to accommodate at least a portion of the upper surface of the microneedle electrode array from which the microneedles extend. Each of the conductive pads is disposed in electrical communication with a corresponding one of the plurality of microneedle electrode arrays and the first and second substrate are bonded together such that each one of the plurality of microneedle electrode arrays extends through a corresponding one of the plurality of openings defined in the second substrate.

U.S. Pat. No. 8,308,960 for Methods for Making Microneedles and Applications Thereof discloses a method of making vertically protruding elements on a substrate, said elements having a tip comprising at least one inclined surface and an elongated body portion extending between said substrate and said tip. The method comprises an anisotropic, crystal plane dependent etch forming said inclined surface(s); and an anisotropic, non crystal plane dependent etch forming said elongated body portion; combined with suitable patterning processes defining said protruding elements to have a predetermined base geometry.

U.S. Pat. No. 8,637,351 for Methods for Making Microneedles and Applications Thereof discloses a method of making vertically protruding elements on a substrate, said elements having a tip comprising at least one inclined surface and an elongated body portion extending between said substrate and said tip. The method comprises an anisotropic, crystal plane dependent etch forming said inclined surface(s); and an anisotropic, non crystal plane dependent etch forming said elongated body portion; combined with suitable patterning processes defining said protruding elements to have a predetermined base geometry.

BRIEF SUMMARY OF THE INVENTION

The current solution teaches of a means to implement a spatially-defined, conductive conduit between the sensing surface of a microneedle (or array of microneedles) located on a planar substrate and the opposing surface of said substrate. In doing so, the need to make ohmic contact with the microneedle-containing surface of the substrate is mitigated, which enables unobstructed insertion of the said microneedle (or array of microneedles) into the viable epidermis or dermis.

The technology described herein involves a method for circumscribing an insulating barrier region around a singular conductive microneedle structure or plurality of conductive microneedle structures adhered to a fixed substrate for the purpose of spatially defining a conduit for the routing of an electrical signal from the surface of said microneedle or microneedles to the posterior surface of said substrate.

One aspect of the present invention is a microneedle-based electrochemical biosensors structure. The structure comprises a substrate, a microneedle biosensor, a primary electrically conductive element, a secondary electrically conductive element and an electrically insulative annular barrier. The substrate is composed of an electrically conducting material, the substrate comprising an anterior surface and a posterior surface. The microneedle biosensor has a length ranging from 20 microns to 2000 microns. The microneedle biosensor comprises a penetrating end and a posterior end. The microneedle biosensor protrudes from the anterior surface of the substrate and having a portion within the substrate. The primary electrically conductive element is located on the penetrating end of the microneedle biosensor. The secondary electrically conductive element is located on the posterior end of the microneedle biosensor. The electrically insulative annular barrier surrounds the portion of microneedle biosensor that is embedded in the substrate to electrically isolate the microneedle biosensor from the substrate.

Another aspect of the present invention is a microneedle-based electrochemical biosensors structure. The structure comprises a substrate, a plurality of microneedle biosensors, a primary electrically conductive element, a secondary electrically conductive element and an electrically insulative annular barrier. The substrate is composed of an electrically conducting material, the substrate comprising an anterior surface and a posterior surface. Each of the plurality of microneedle biosensors has a length ranging from 20 microns to 2000 microns. Each microneedle biosensor comprises a penetrating end and a posterior end, each microneedle biosensor protruding from the anterior surface of the substrate and having a portion within the substrate. The primary electrically conductive element is located on the penetrating end of each microneedle biosensor. The secondary electrically conductive element is located on the posterior end of each microneedle biosensor. The electrically insulative annular barrier surrounds the portion of each microneedle biosensor that is embedded in the substrate to electrically isolate the microneedle biosensor from the substrate.

Yet another aspect of the present invention is a microneedle-based electrochemical biosensors structure with a printed circuit board (PCB). The structure comprises a PCB, a substrate, a plurality of microneedle biosensors, a primary electrically conductive element, a secondary electrically conductive element, an electrically insulative annular barrier and a plurality of phase-change conductive interconnects. The PCB comprises a pad, at least one via and a plurality of traces. The substrate is composed of an electrically conducting material, the substrate comprising an anterior surface and a posterior surface. Each of the plurality of microneedle biosensors has a length ranging from 20 microns to 2000 microns. Each microneedle biosensor comprises a penetrating end and a posterior end, each microneedle biosensor protruding from the anterior surface of the substrate and having a portion within the substrate. The primary electrically conductive element is located on the penetrating end of each microneedle biosensor. The secondary electrically conductive element is located on the posterior end of each microneedle biosensor. The electrically insulative annular barrier surrounds the portion of each microneedle biosensor that is embedded in the substrate to electrically isolate the microneedle biosensor from the substrate. The phase-change conductive interconnect is positioned between the pad of the printed circuit board and the secondary electrically conductive element.

Yet another aspect of the present invention is a microneedle-based electrochemical biosensors structure with a printed circuit board (PCB). The structure comprises a PCB, a substrate, a microneedle biosensor, a primary electrically conductive element, a secondary electrically conductive element, an electrically insulative annular barrier and a plurality of phase-change conductive interconnects. The PCB comprises a pad, at least one via and a plurality of traces. The substrate is composed of an electrically conducting material, the substrate comprising an anterior surface and a posterior surface. Each of the plurality of microneedle biosensors has a length ranging from 20 microns to 2000 microns. Each microneedle biosensor comprises a penetrating end and a posterior end, each microneedle biosensor protruding from the anterior surface of the substrate and having a portion within the substrate. The primary electrically conductive element is located on the penetrating end of each microneedle biosensor. The secondary electrically conductive element is located on the posterior end of each microneedle biosensor. The electrically insulative annular barrier surrounds the portion of each microneedle biosensor that is embedded in the substrate to electrically isolate the microneedle biosensor from the substrate. Each of the phase-change conductive interconnects is positioned between the pad of the printed circuit board and the secondary electrically conductive element of each microneedle biosensor.

Yet another aspect of the invention is the jetting of solder balls, spheres, or solder bumps onto the secondary conductive element on located on the posterior end of each microneedle biosensor to facilitate solder reflow with pads located on the IC, IC package, chip carrier, or PCB. Said solder balls, spheres, or solder bumps may be simultaneously jetted onto the secondary conductive element and heated by means of a reflow laser to facilitate adhesion of said solder balls, spheres, or solder bumps onto the underlying secondary conductive element. Optionally, said process can be implemented on a wafer scale or by means of wafer-level solder balling to accelerate the rate at which said jetting occurs. In such a process, solder balls, spheres, or solder bumps are attached, simultaneously, to all the secondary conductive elements located on the posterior ends of each microneedle biosensor on a wafer substrate in a highly parallelized fashion.

Yet another aspect of the invention is the attachment of an electrically-conductive epoxy to at least one of a secondary conductive element on located on the posterior end of each microneedle biosensor and a pad located on an IC, IC package, chip carrier, or PCB. Optionally, heat can be employed to reflow the electrically-conductive epoxy. Optionally, the electrically-conductive epoxy can cure following UV exposure. Optionally, the electrically-conductive epoxy can cure following remaining at ambient conditions for a defined period of time.

Yet another aspect of the invention is the incorporation of a conducting metallic pillar into the solder ball, sphere, or bump to increase the standoff between the secondary electrically conductive element located on the posterior end of each microneedle biosensor and the underlying pad located on the surface of an IC, IC package, chip carrier, or PCB.

Yet another aspect of the invention is the selection of the secondary conductive element on located on the posterior end of each microneedle biosensor to facilitate stud bumping or the attachment of solder balls. Said conductive element can be selected from, for example, gold, nickel, aluminum, and palladium or be comprised of a bi- or tri-metallic alloy of any permutation of the same.

Yet another aspect of the invention is the selection of the pad material located on the IC, IC package, chip carrier, or PCB. The selection of the material is to facilitate stud bumping or the attachment of solder balls. Said pad material can be selected from, for example, gold, nickel, aluminum, and palladium or be comprised of a bi- or tri-metallic alloy of any permutation of the same.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
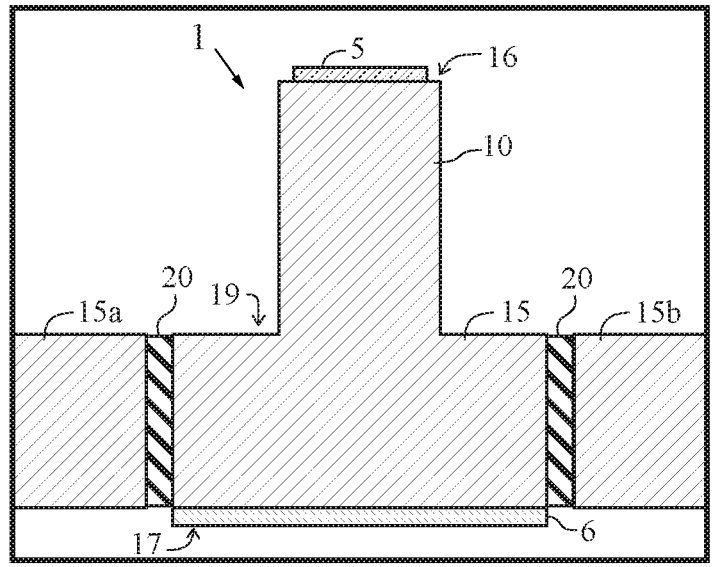
FIG. 1 is a cross-sectional view of a singular electrically-conductive microneedle structure located on the anterior surface of an electrically-conductive substrate.

The technology disclosed herein addresses the above challenge via the implementation of fully-insulating barriers that circumscribe and thereby electrically isolate the microneedle (or plurality of microneedles) from other locations on the substrate. In this manner, an electrical signal can be routed from a spatially-defined electrically-conductive region located on the tip of the microneedle (or plurality of microneedles) to the posterior surface of the substrate to facilitate probing and device-level packaging while leaving the surface containing the microneedle(s) exposed to enable skin penetration and subsequent sensing operation. An electrically-conductive substrate (i.e. semiconductor wafer, polymer wafer, glass wafer, ceramic wafer, or metal wafer) containing microneedles on the anterior surface (each microneedle featuring a primary electrically-conductive element (i.e. metal, semiconductor, conducting polymer) in ohmic contact with the conductive substrate) and a secondary electrically-conductive element (i.e. metal, semiconductor, conducting polymer) on the posterior surface undergoes an etching process whereby substrate material in an annular region circumscribing one or more conductive microneedles is removed. The trench created in this process, which must be less than the thickness of the substrate, is filled with an insulating material (growth of a native oxide or deposition of an electrically-insulating compound). The substrate is then flipped to expose the opposing surface and another trench (having identical geometric features to the aforementioned trench) is etched to a depth sufficient to access the opposing filled trench. This trench is subsequently filled with an insulating material (growth of a native oxide or deposition of an electrically-insulating compound). In this fashion, an isolated, electrically-conducting region extending from the primary electrical contact (located on or within the microneedle structure) to the secondary electrical contact is realized. The secondary electrically-conductive element is either probed directly, bonded to solder bumps and exposed to solder reflow to attach to pads populating a printed circuit board (PCB), or bonded to solder bumps located within an integrated circuit package. The IC package can be probed directly, placed in a socket, or soldered onto a printed circuit board to facilitate electrochemical analysis (control of the redox reaction and readout of the signal). This approach is in direct analogy to conductive through-silicon vias implemented in silicon-based semiconductor substrates, which are widely used in 3-dimensional semiconductor manufacturing and wafer-level packaging. The differentiating feature in the current innovation resides in the approach of 'filling' the via with insulating material and circumscribing an enclosed region with said via to facilitate full electrical isolation from other portions of the substrate not located within the enclosed region.

The structure preferably includes a substrate, a microneedle biosensor, a primary electrically-conductive element, a secondary electrically-conductive element, and an electrically-insulative annular barrier. The substrate is fabricated from an intrinsically conducting or semiconducting material (i.e. doped semiconductor wafer, conducting polymer wafer, glass wafer, ceramic wafer, or metal wafer). The substrate features anterior and posterior surfaces. The microneedle biosensor is a defined protrusion from the anterior surface of the substrate possessing vertical extent of between 20 and 2000 μm and designed to penetrate the stratum corneum or other biological tissue to access a viable physiological fluid (such as blood, plasma, serum, or interstitial fluid). The primary electrically-conductive element is a defined conductive region located on the surface of said microneedle structure, intended to react, either directly or indirectly, with a chemical analyte in the physiological medium. The secondary electrically-conductive element is a defined conductive region located on the posterior surface of said substrate, intended to enable ohmic contact with a electrical probing mechanism or bonding/soldering to an integrated circuit package or printed circuit board. The electrically-insulative annular barrier is an annular barrier, defined via an etching, milling, machining, ablative, or otherwise subtractive processes, filled with an electrically insulating material to spatially define a region of conductivity within the annulus and provide isolation with the substrate located to the exterior of said annulus. The electrically insulating material can be filled by means of the oxidative growth of a native, non-conducting oxide, nitride, or other alloy or the additive deposition of the same.

The method for manufacturing the structure includes etching, milling, machining, or ablating of an anterior trench in which an etching process is used on the anterior surface of a conductive substrate to remove material in a defined patterned region, thereby defining an anterior trench. The method also includes implementation of an insulating material in anterior trench in which an insulating layer is grown or deposition of an insulating material in said anterior trench. The method also includes etching, milling, machining, or ablating of the posterior trench in which one of the etching, milling, machining, or ablating process is used on the posterior surface of said conductive substrate to remove material in a defined patterned region, thereby defining a posterior trench. Substrate material is etched, milled, machined, or ablated to a depth that is equal to or greater than the difference between the substrate thickness and the depth of the anterior trench, but less than the overall thickness of the substrate. The method also includes implementation of an insulating material in posterior trench in which an insulating layer is grown or deposition of an insulating material in said posterior trench.

Figure 1A:
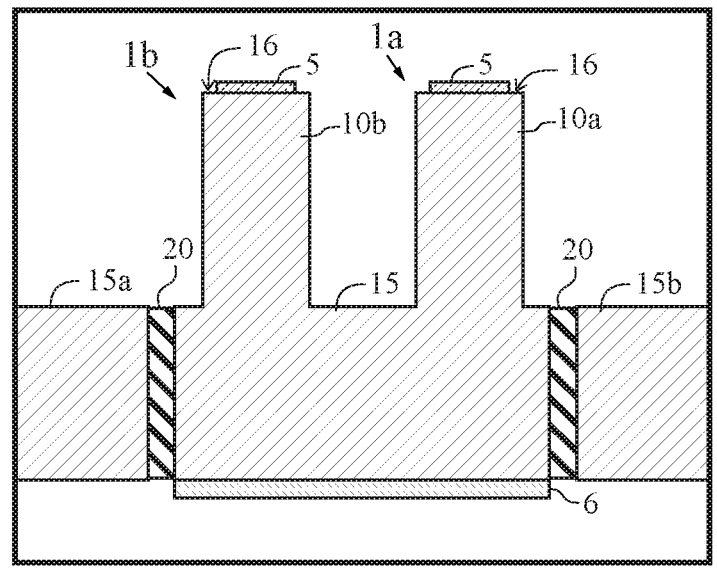
FIG. 1A is a cross-sectional view of multiple microneedle structures located on the anterior surface of an electrically-conductive substrate.

FIGS. 1 and 1A illustrate a singular electrically-conductive microneedle structure 1 and a plurality of microneedle structures 1a and 1b located on the anterior surface 16 of an electrically-conductive substrate 15. Insulating barriers 20 are shown and possess a vertical extent equal to the thickness of the substrate 15. A primary electrically-conductive sensing element 5 is located on the microneedle structure 10 and a secondary electrically-conductive probing element (pad) 6 is located on the posterior surface 17 of the substrate 15. The substrate 15 is preferably selected from the group consisting of a semiconductor wafer, a rigid polymer, a flexible polymer, glass, ceramic, or metal. The electrically conductive element 5 and 6 preferably includes a metal, doped region of semiconductor, or conducting polymer. The microneedle 10 comprises a protrusion of vertical extent of between 20 and 2000 μm from the base 19 of the substrate 15 and designed to penetrate a biological interface.

Figure 2:
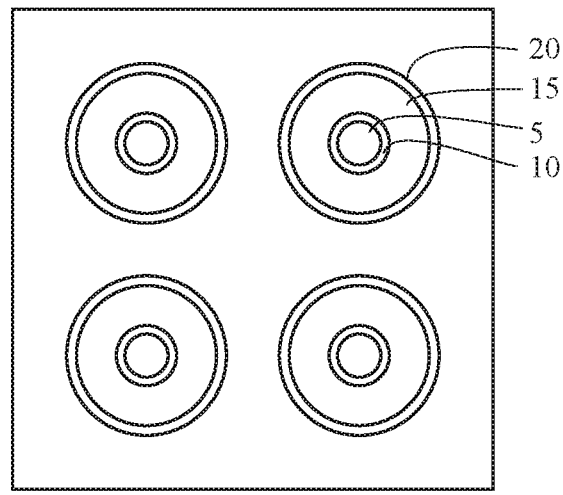
FIG. 2 is a top plan view of an anterior surface of a substrate featuring a microneedle element circumscribed by an insulating barrier.
Figure 2A:
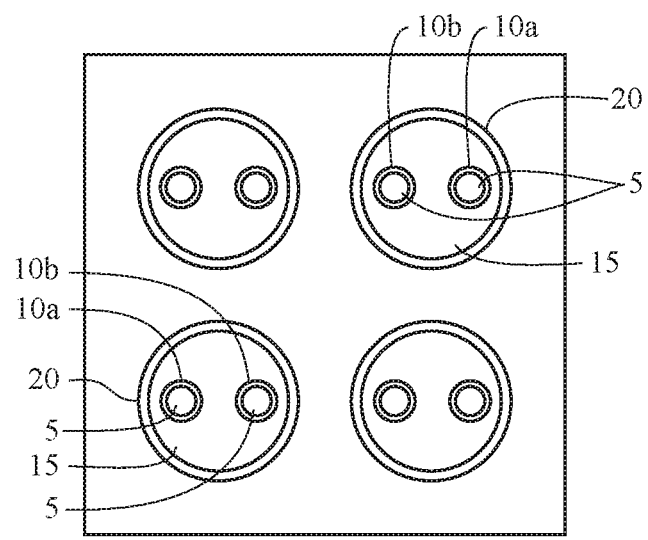
FIG. 2A is a top plan view of an anterior surface of a substrate featuring microneedle elements circumscribed by an insulating barrier.

FIGS. 2 and 2A illustrate top plan views of the anterior surface 16 of the substrate 15 featuring the microneedle element 10 or elements 10a and 10b circumscribed by an insulating barrier 20.

Figure 3:
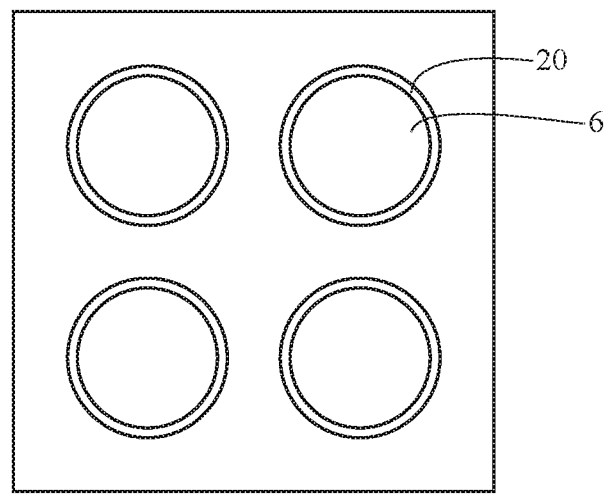
FIG. 3 is a view of a posterior surface of a substrate featuring a secondary electrically-conductive element (pad) circumscribed by an insulating barrier.

FIG. 3 is a view of the posterior surface 17 of the substrate 17 featuring the secondary electrically-conductive element (pad) 6 circumscribed by an insulating barrier 20.

Figure 4:
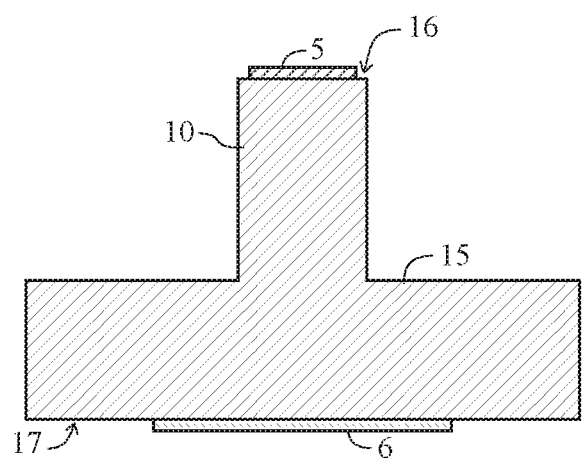
FIG. 4 is a preliminary phase of a fabrication process implemented to define insulating barrier regions to electrically isolate a microneedle and underlying substrate to facilitate electrical probing from the posterior surface of the substrate.
Figure 4A:
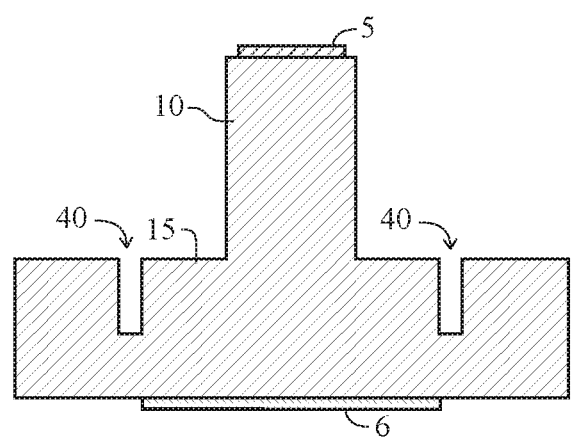
FIG. 4A is a first step of the fabrication process in which a substrate is etched from a single side.
Figure 4B:
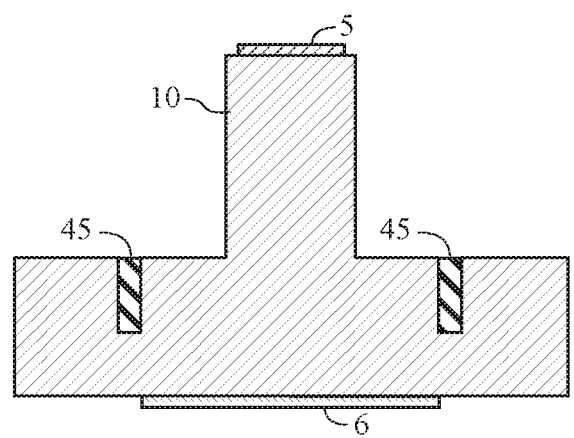
FIG. 4B is a second step of the fabrication process in which the etched void is filled with an insulating material.
Figure 4C:
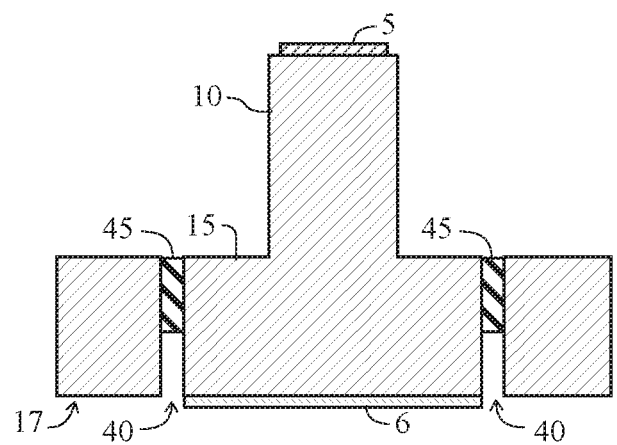
FIG. 4C is a third step of the fabrication process in which an opposing side of the substrate is etched.
Figure 4D:
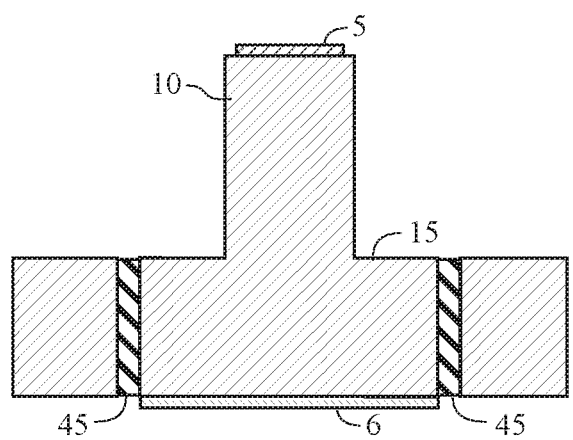
FIG. 4D is a fourth step of the fabrication process in which the opposing side void is filled with an insulating material.

FIGS. 4, 4A, 4B, 4C and 4D illustrate a preferred fabrication process implemented to define insulating barrier regions to electrically isolate the microneedle and underlying substrate to facilitate electrical probing from the posterior surface of the substrate. As shown in FIG. 4, a substrate 15 has a microneedle 10 extending upward. A primary electrically-conductive sensing element 5 is located on an anterior surface 16 of the microneedle structure 1 and a secondary electrically-conductive probing element (pad) 6 is located on the posterior surface 17 of the substrate 15. As shown in FIG. 4, voids 40 are etched from the substrate 15. As shown in FIG. 4B, insulating material 45 fills the voids 40. As shown in FIG. 4C, voids 40 are etched from a posterior surface 17 of the substrate 15. As shown in FIG. 4D, insulating material 45 fills the voids 40 in the posterior surface 17 of the substrate 15.

Figure 5:
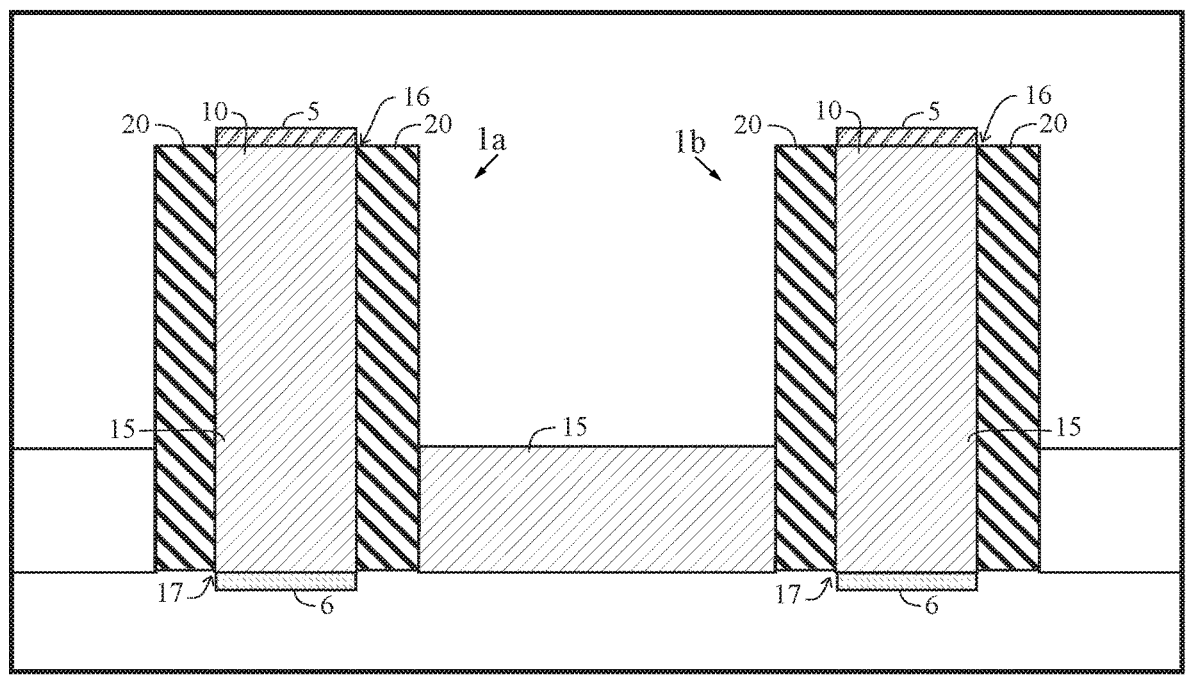
FIG. 5 is a cross-sectional view of singular electrically-conductive microneedle structures, electrically-isolated from one another, and located on the anterior surface of an electrically-conductive substrate.

FIG. 5 is a cross-sectional view of a singular electrically-conductive microneedle structures 1a and 1b, electrically-isolated from one another, located on the anterior surface of an electrically-conductive substrate 15. Insulating barriers 20 are shown and possess a vertical extent equal to the sum of the thickness of the substrate 15 and the height of the microneedle 10. A primary electrically-conductive sensing element 5 is located on the distal extent of the microneedle 10 and a secondary electrically-conductive probing element (pad) 6 is located on the posterior surface 17 of the substrate 15, directly underneath the primary electrically-conductive sensing element 6.

Figure 6:
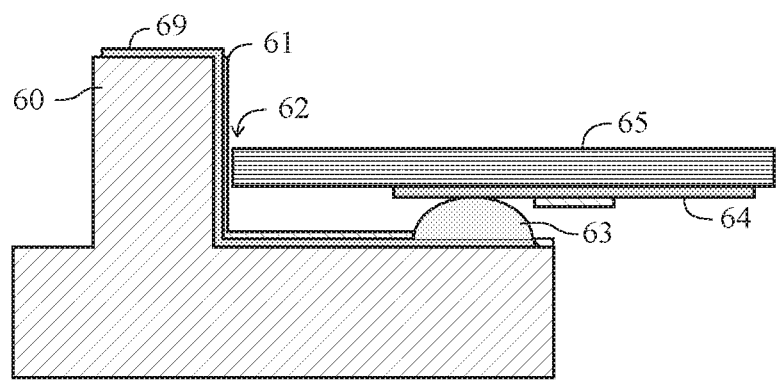
FIG. 6 is a cross-sectional view of a prior art flip-chip bonding configuration and method of interface.
Figure 6A:
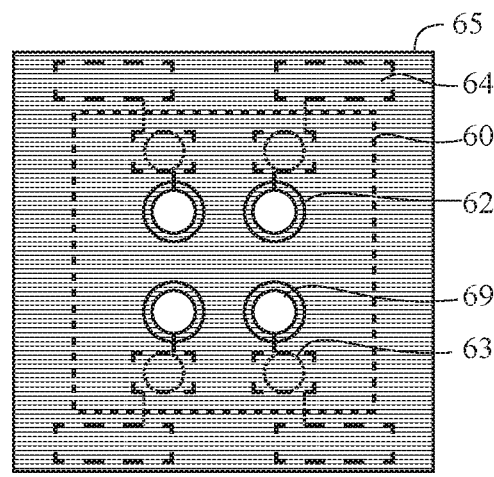
FIG. 6A is a top plan view of a prior art packaged microneedle sensing device.

FIGS. 6 and 6A illustrate the prior art flip-chip bonding configuration and method of interface of a packaged microneedle sensing device. A substrate 60 has a metal surface trace 69, a surface insulation 61, an opening for a microneedle 62, a package substrate/housing 65, a flip chip bond 63 and an external package connection pad/connect 64.

Figure 7:
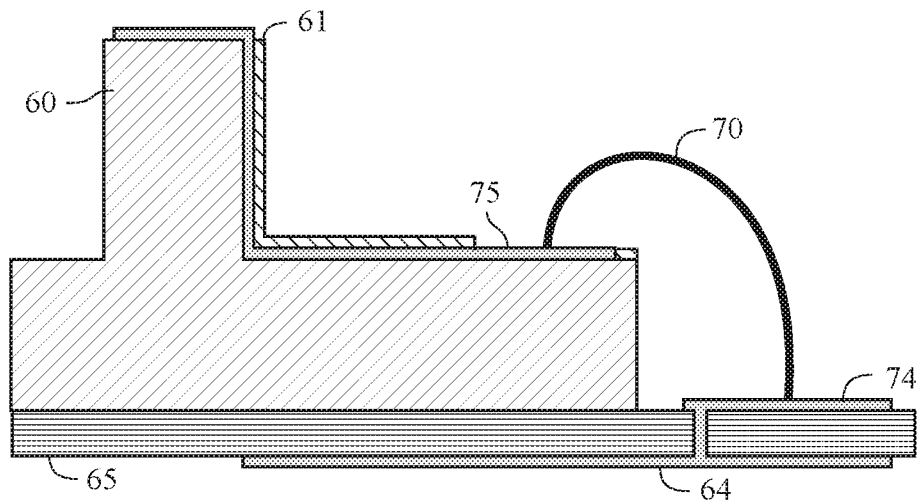
FIG. 7 is a cross-sectional view of the prior art wire bonding configuration and method of interface.
Figure 7A:
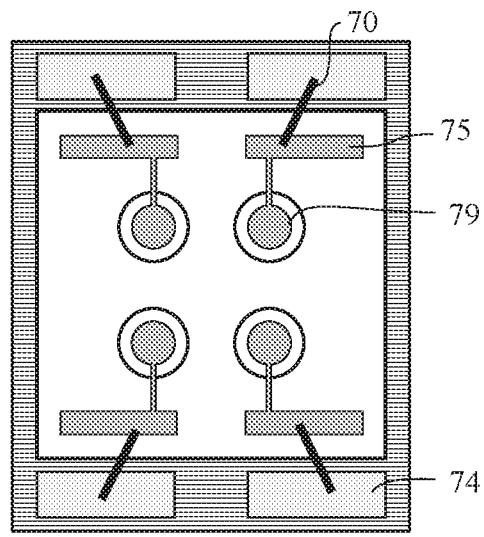
FIG. 7A is a top plan view of a prior art packaged microneedle sensing device.

FIGS. 7 and 7A illustrate the prior art wire bonding configuration and method of interface of a packaged microneedle sensing device. A substrate 60 has a metal surface trace 75, a surface insulation 61, a package substrate/housing 65, a wire bond 70, an external package connection pad/connect 64, and an internal package contact 74.

Figure 8:
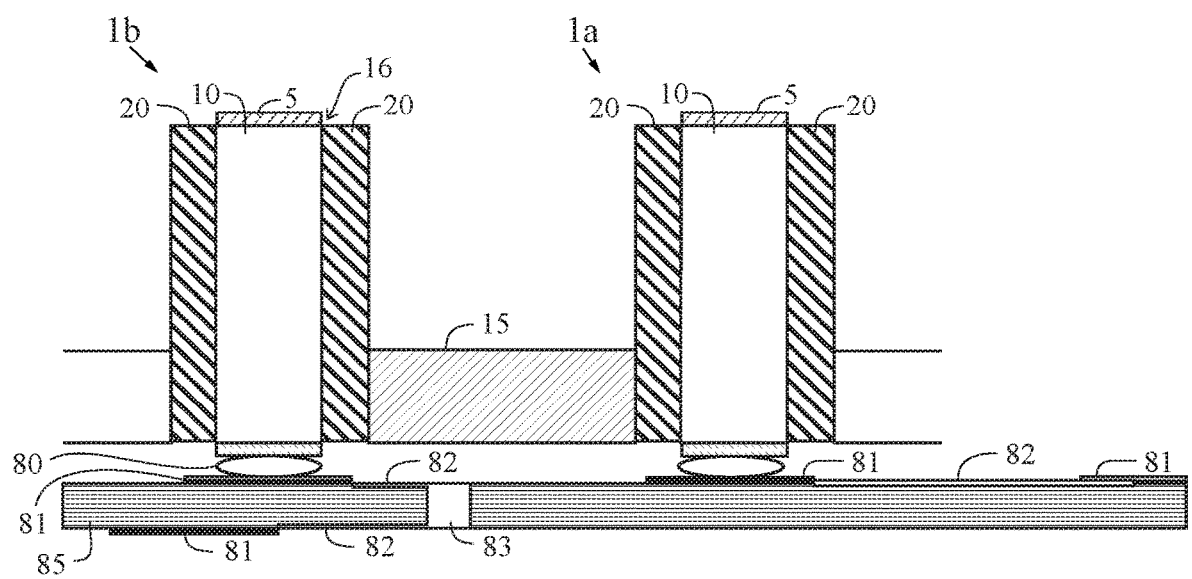
FIG. 8 is a cross-sectional view of two electrically-isolated microneedles occupying the same substrate to illustrate a solder ball/stud bumping configuration and method of interface.

FIG. 8 is an illustration of a solder ball/stud bumping configuration and method of interface. Two electrically-isolated microneedle structures 1a and 1b occupying the same substrate 15, one structure 1b of which is mounted and interfaced using a via 83 between two opposing pads 81a and 81b to gain electrical access to the primary electrically-conductive element 5 on the posterior surface of the printed circuit board/package/chip carrier 85, and the other structure 1a of which is mounted and interfaced using two offset pads 81c and 81d connected by a trace 82 to gain electrical access to the primary electrically-conductive element 5 on the anterior surface 16 of the printed circuit board/package/chip carrier 85.

One embodiment is a microneedle-based electrochemical biosensors structure 1 with a printed circuit board (PCB) 85. The structure 1 comprises a PCB 85, a substrate 15, a microneedle biosensor 10, a primary electrically conductive element 5, a secondary electrically conductive element 6, an electrically insulative annular barrier 20 and a plurality of phase-change conductive interconnects. The phase-change conductive interconnect is preferably one of a solder ball 80 and a conductive epoxy. The PCB 85 comprises a pad 81, at least one via 83 and a plurality of traces 82. The substrate 15 is preferably composed of an electrically conducting material. The substrate preferably comprises an anterior surface 16 and a posterior surface 17. Each of the plurality of microneedle biosensors 10 has a length ranging from 20 microns to 2000 microns. Each microneedle biosensor 10 comprises a penetrating end and a posterior end. Each microneedle biosensor 10 protrudes from the anterior surface 16 of the substrate 15 and has a portion within the substrate 15. The primary electrically conductive element 5 is located on the penetrating end of each microneedle biosensor 10. The secondary electrically conductive element 6 is located on the posterior end of each microneedle biosensor 10. The electrically insulative annular barrier 20 surrounds the length of each microneedle biosensor 10 to electrically isolate the microneedle biosensor 10 from the substrate 15. Each of the phase-change conductive interconnects 80 is positioned between the pad 81 of the PCB 85 and the secondary electrically conductive element 6 of each microneedle biosensor 10.

The secondary electrically conductive element 6 is preferably composed of a metal, a doped region of semiconductor, or a conducting polymer.

Each microneedle biosensor 10 is preferably configured to penetrate a stratum corneum of a mammal.

The biological interface is preferably a stratum corneum.

The substrate 15 is preferably composed of a semiconductor wafer, a rigid polymer, a flexible polymer, a glass material, a ceramic material, or a metal material.

McCanna et al., U.S. patent application Ser. No. 14/843,926, filed on Sep. 2, 2015, for a Miniaturized Sub-Nano-ampere Sensitivity Low-Noise Potentiostat System is hereby incorporated by reference in its entirety.

Windmiller et al., U.S. patent application Ser. No. 14/955,850, filed on Dec. 1, 2015, for a Method And Apparatus For Determining Body Fluid Loss is hereby incorporated by reference in its entirety.

Windmiller, U.S. patent application Ser. No. 15/177,289, filed on Jun. 8, 2016, for a Methods And Apparatus For Interfacing A Microneedle-Based Electrochemical Biosensor With An External Wireless Readout Device is hereby incorporated by reference in its entirety.

Wang et al., U.S. Patent Publication Number 20140336487 for a Microneedle Arrays For Biosensing And Drug Delivery is hereby incorporated by reference in its entirety.

Windmiller, U.S. patent application Ser. No. 15/590,105 for a Tissue-Penetrating Electrochemical Sensor Featuring A Co Electrodeposited Thin Film Comprised Of A Polymer And Bio-Recognition Element is hereby incorporated by reference in its entirety.

PCT Application Number PCT/US17/55314 for an Electro-Deposited Conducting Polymers For The Realization Of Solid-State Reference Electrodes For Use In Intracutaneous And Subcutaneous Analyte-selective Sensors is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A biosensor, comprising:
   a substrate comprising an electrically conducting material;
   a microneedle within the substrate and having a portion extending from an anterior surface of the substrate, the extending portion comprising a penetrating end of the microneedle;
   a primary electrically conductive element located on the penetrating end of the microneedle;
   a secondary electrically conductive element located on a posterior end of the microneedle; and
   an electrically insulative barrier surrounding a length of the microneedle between the primary electrically conductive element and the secondary electrically conductive element,
   wherein the electrically insulative barrier electrically isolates the microneedle from the substrate.

2. The biosensor of claim 1, wherein the substrate comprises a semiconductor, a rigid conducting polymer, a flexible conducting polymer, or a metal.

3. The biosensor of claim 1, wherein the primary electrically conductive element comprises a metal, a doped region of semiconductor, or a conducting polymer.

4. The biosensor of claim 1, wherein the secondary electrically conductive element comprises a metal, a doped region of semiconductor, or a conducting polymer.

5. The biosensor of claim 1, wherein the electrically insulative barrier circumscribes the secondary electrically conductive element.

6. The biosensor of claim 1, wherein the microneedle is configured to penetrate a stratum corneum of a mammal.

7. The biosensor of claim 1, wherein the extending portion comprises a columnar body and the penetrating end of the microneedle.

8. The biosensor of claim 7, wherein the penetrating end is at a distal end of the microneedle and is separated from the anterior surface of the substrate by a length of the columnar body.

9. The biosensor of claim 1, wherein the microneedle is formed from the electrically conducting material of the substrate.

10. The biosensor of claim 1, wherein the primary electrically conductive element comprises an analyte sensing element.

11. A biosensor, comprising:
a substrate comprising an electrically conducting material;
a plurality of microneedles within the substrate, each microneedle having a portion extending from an anterior surface of the substrate, each extending portion comprising a penetrating end of a respective microneedle;
a plurality of primary electrically conductive elements, each one located on the penetrating end of a respective microneedle of the plurality of microneedles;
a plurality of secondary electrically conductive elements, each one located on a posterior end of a respective microneedle of the plurality of microneedles; and
a plurality of electrically insulative barriers, each one surrounding a length of a respective microneedle of the plurality of microneedles between a primary electrically conductive element and a corresponding secondary electrically conductive element,
wherein each of the plurality of electrically insulative barriers electrically isolates a respective microneedle from the substrate.

12. The biosensor of claim 11, wherein the substrate comprises a semiconductor, a rigid conducting polymer, a flexible conducting polymer, or a metal.

13. The biosensor of claim 11, wherein each of the primary electrically conductive elements comprises a metal, a doped region of semiconductor, or a conducting polymer.

14. The biosensor of claim 11, wherein each of the secondary electrically conductive elements comprises a metal, a doped region of semiconductor, or a conducting polymer.

15. The biosensor of claim 11, wherein each of the electrically insulative barriers circumscribes a corresponding secondary electrically conductive element of a respective microneedle.

16. The biosensor of claim 11, wherein each of the plurality of microneedles is configured to penetrate a stratum corneum of a mammal.

17. The biosensor of claim 11, wherein, for each microneedle of the plurality of microneedles, the extending portion comprises a columnar body and a respective penetrating end of the microneedle.

18. The biosensor of claim 17, wherein the penetrating end is at a distal end of each microneedle and is separated from the anterior surface of the substrate by a length of the respective columnar body.

19. The biosensor of claim 11, wherein each microneedle of the plurality of microneedles is formed from the electrically conducting material of the substrate.

20. The biosensor of claim 11, wherein each primary electrically conductive element of the plurality of primary electrically conductive elements comprises an analyte sensing element.

21. A biosensor, comprising:
a substrate comprising an electrically conducting material;
a microneedle within the substrate and having a portion extending from an anterior surface of the substrate, the extending portion comprising a columnar body and a penetrating end of the microneedle;
a primary electrically conductive element located on the penetrating end of the microneedle;
a secondary electrically conductive element located on a posterior end of the microneedle; and
an electrically insulative barrier surrounding the microneedle within the substrate and along the columnar body portion,
wherein the electrically insulative barrier electrically isolates the microneedle from the substrate.

22. The biosensor of claim 21, wherein the substrate comprises a semiconductor, a rigid conducting polymer, a flexible conducting polymer, or a metal.

23. The biosensor of claim 21, wherein the primary electrically conductive element comprises a metal, a doped region of semiconductor, or a conducting polymer.

24. The biosensor of claim 21, wherein the secondary electrically conductive element comprises a metal, a doped region of semiconductor, or a conducting polymer.

25. The biosensor of claim 21, wherein the electrically insulative barrier circumscribes the secondary electrically conductive element.

26. The biosensor of claim 21, wherein the microneedle is configured to penetrate a stratum corneum of a mammal.

27. The biosensor of claim 21, wherein the penetrating end is at a distal end of the microneedle and is separated from the anterior surface of the substrate by a length of the columnar body.

28. The biosensor of claim 21, wherein the microneedle is formed from the electrically conducting material of the substrate.

29. The biosensor of claim 21, wherein the primary electrically conductive element comprises an analyte sensing element.

30. A biosensor, comprising:
a substrate comprising an electrically conducting material;
a plurality of microneedles within the substrate, each microneedle having a portion extending from an anterior surface of the substrate, each extending portion comprising a columnar body and a penetrating end of a respective microneedle;
a plurality of primary electrically conductive elements, each one located on the penetrating end of a respective microneedle of the plurality of microneedles;
a plurality of secondary electrically conductive elements, each one located on a posterior end of a respective microneedle of the plurality of microneedles; and
a plurality of electrically insulative barriers, each one surrounding a respective microneedle within the substrate and along a respective columnar body portion,
wherein each of the plurality of electrically insulative barriers electrically isolates a respective microneedle from the substrate.

* * * * *